US009730658B2

(12) United States Patent
Tajima et al.

(10) Patent No.: US 9,730,658 B2
(45) Date of Patent: Aug. 15, 2017

(54) RADIOGRAPHIC IMAGING APPARATUS AND ELECTRONIC CASSETTE

(71) Applicant: FUJIFILM Corporation, Tokyo (JP)

(72) Inventors: Takashi Tajima, Ashigarakami-gun (JP); Tetsuya Tsuji, Ashigarakami-gun (JP); Haruyasu Nakatsugawa, Ashigarakami-gun (JP); Yoshihisa Hirano, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/146,072

(22) Filed: May 4, 2016

(65) Prior Publication Data
US 2016/0345920 A1 Dec. 1, 2016

(30) Foreign Application Priority Data
May 29, 2015 (JP) .................................. 2015-109583

(51) Int. Cl.
| A61B 6/00 | (2006.01) |
| G01T 1/24 | (2006.01) |
| G03B 42/00 | (2006.01) |
| G01T 1/20 | (2006.01) |

(52) U.S. Cl.
CPC .......... *A61B 6/4283* (2013.01); *A61B 6/4405* (2013.01); *A61B 6/5294* (2013.01); *A61B 6/547* (2013.01); *A61B 6/563* (2013.01); *G01T 1/2018* (2013.01); *G01T 1/24* (2013.01); *G01T 1/247* (2013.01); *G03B 42/00* (2013.01)

(58) Field of Classification Search
CPC ... A61B 6/4283; A61B 6/4405; A61B 6/5294; A61B 6/547; A61B 6/563; G01T 1/2018; G01T 1/24; G01T 1/247; G03B 42/00
See application file for complete search history.

(56) References Cited

U.S. PATENT DOCUMENTS

| 2012/0206233 A1* | 8/2012 | Kamiya | ............... A61B 6/4283 340/2.1 |
| 2015/0078522 A1* | 3/2015 | Makino | ................. A61B 6/563 378/62 |
| 2016/0358458 A1* | 12/2016 | Kudo | .................. G08B 29/185 |

FOREIGN PATENT DOCUMENTS

JP    2013-039322 A    2/2013

* cited by examiner

Primary Examiner — Mark R Gaworecki
(74) Attorney, Agent, or Firm — Sughrue Mion, PLLC

(57) ABSTRACT

In a radiographic imaging apparatus, a radiation image of an object is detected by use of one of first and second electronic cassettes, to input the radiation image to the console device. The first electronic cassette is changed over between a normal transmission mode and a relay transmission mode. In the normal transmission mode, the radiation image is transmitted through a path from the first electronic cassette to the console device, and in the relay transmission mode, the radiation image is transmitted from the first electronic cassette to the second electronic cassette wirelessly and then from the second electronic cassette to the console device. Transmission of a radiation image can be performed reliably without unwanted interruption, because an indirect path of the relay transmission mode can be used even upon occurrence of a technical problem of inefficiency in the normal transmission mode.

15 Claims, 30 Drawing Sheets

FIG. 3

| REQUEST FOR IMAGING | REQUEST ID | OD0001 |
|---|---|---|
| | CASE ID | P0500 |
| | BODY PART/POSTURE/DIRECTION | CHEST/SITTING/AP |
| | MOBILE IMAGING | YES |

| CASSETTE ID | NAME | OUTER SIZE |
|---|---|---|
| DR0001 | A CASSETTE | 14x17 INCHES |
| DR0002 | B CASSETTE | 17x17 INCHES |
| DR0003 | C CASSETTE | 14x17 INCHES |
| DR0004 | D CASSETTE | 17x17 INCHES |

| IMAGING CONDITION (MENU) | EXPOSURE CONDITION |
|---|---|
| CHEST/LYING/AP | TUBE VOLTAGE 100 kV, TUBE CURRENT 200 mA, EXPOSURE TIME 20 msec |
| CHEST/LYING/PA | TUBE VOLTAGE 120 kV, TUBE CURRENT 220 mA, EXPOSURE TIME 25 msec |
| ABDOMEN/LYING/AP | TUBE VOLTAGE 150 kV, TUBE CURRENT 250 mA, EXPOSURE TIME 25 msec |
| ABDOMEN/LYING/PA | TUBE VOLTAGE 155 kV, TUBE CURRENT 260 mA, EXPOSURE TIME 28 msec |

FIG. 6

| REQUEST ID | CASE ID | ROOM NO | MOBILE IMAGING | CASSETTE ID | IMAGING CONDITION (MENU) | EXPOSURE CONDITION | IMAGE ID |
|---|---|---|---|---|---|---|---|
| OD0001-A | P0500 | 201 | YES | DR0001 | CHEST/ UPRIGHT/AP | TUBE VOLTAGE 100 kV... | FFDR0001 |
| OD0001-B | P0500 | 201 | YES | DR0002 | ABDOMEN/ LYING/AP | TUBE VOLTAGE 150 kV... | FFDR0002 |
| OD0002 | P0600 | 202 | YES | DR0003 | CHEST/LYING/ AP | TUBE VOLTAGE 100 kV... | — |

35

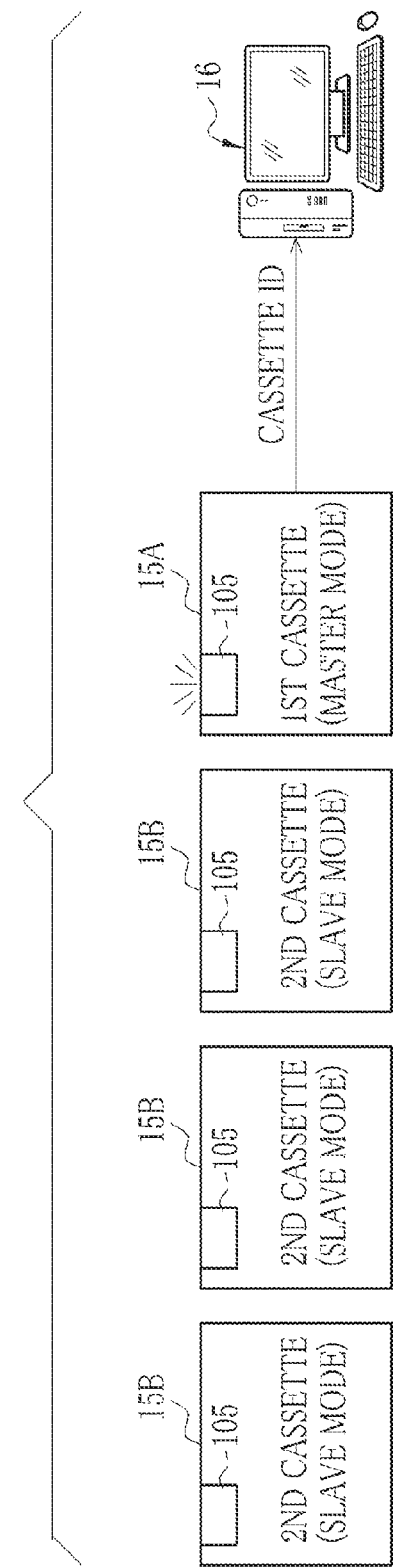

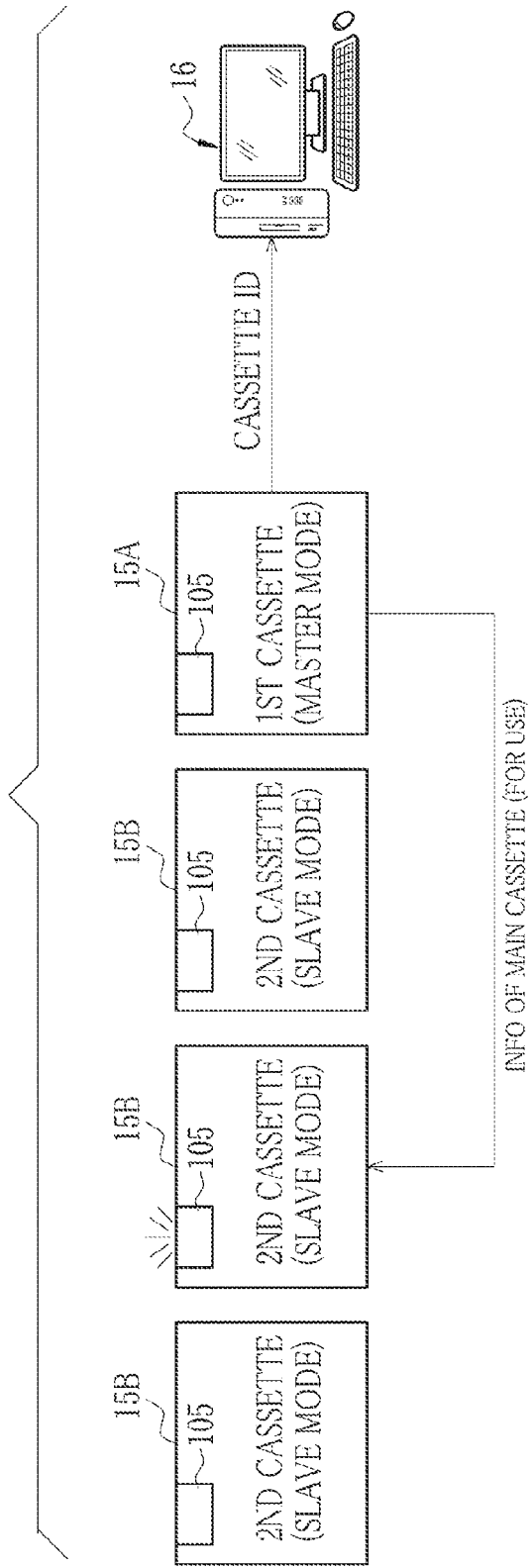

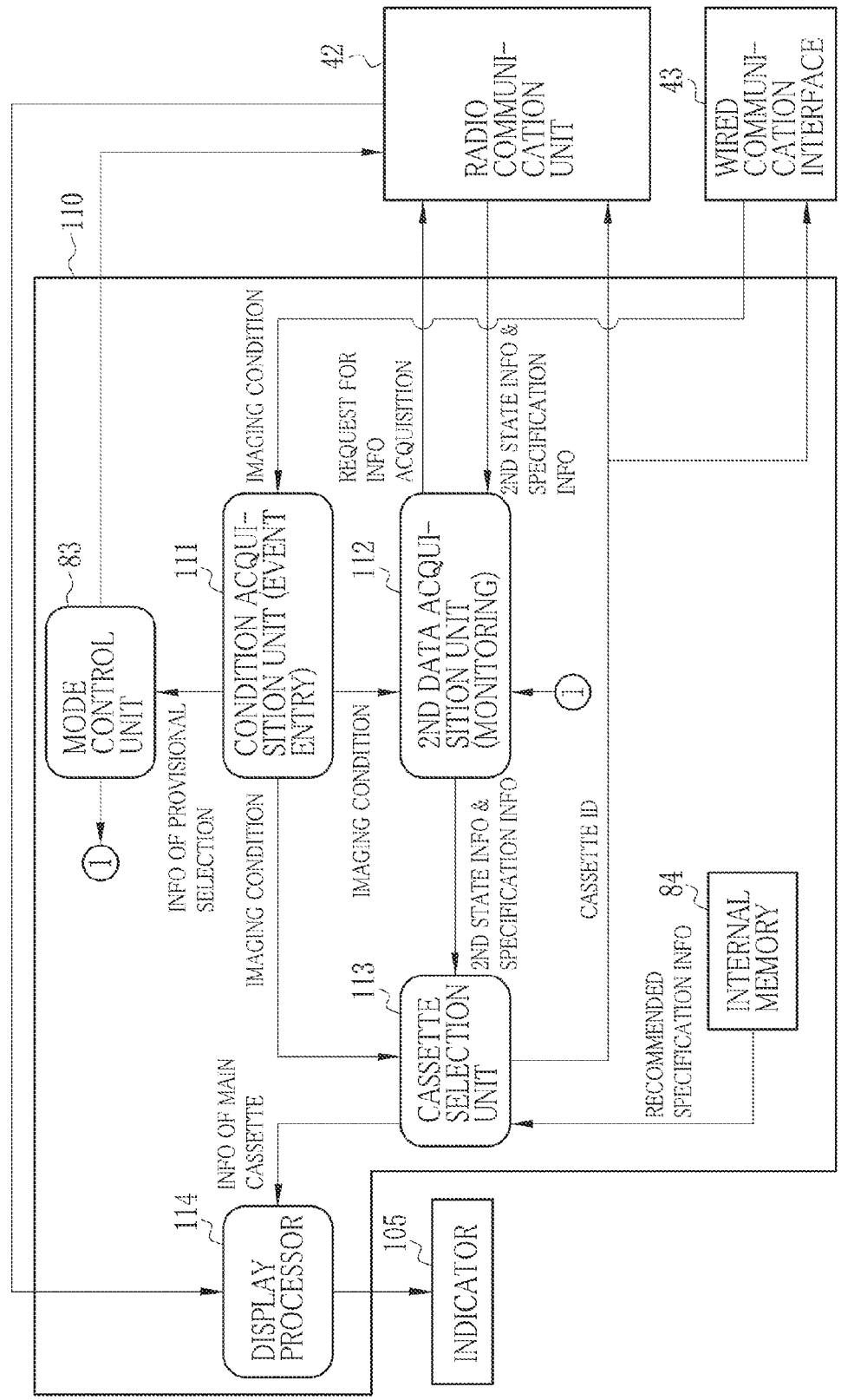

FIG. 29

2ND STATE INFO

| CASSETTE ID | DR0002 |
|---|---|
| AVAILABLE MEMORY SPACE | 200MB |
| AVAILABLE TIME | 40 MIN |
| CUMULATIVE NO OF EVENTS OF IMAGING | 1,200 |
| DATE OF CORRECTION UPDATING FOR OFFSET CORRECTION | 2015.05.08 10:05 |

FIG. 30

SPECIFICATION INFO

| CASSETTE ID | DR0002 |
|---|---|
| OUTER SIZE | 17x17 INCHES |
| PIXEL NO | 2000×2000 |

FIG. 31

RECOMMENDED SPECIFICATION INFO

| IMAGING CONDITION (MENU) | RECOMMENDED SIZE | RECOMMENDED PIXEL NO |
|---|---|---|
| CHEST/LYING/AP | 14x17 INCHES | 1600×2000 |
| CHEST/LYING/PA | 14x17 INCHES | 1600×2000 |
| ABDOMEN/LYING/AP | 17x17 INCHES | 2000×2000 |
| ABDOMEN/LYING/PA | 17x17 INCHES | 2000×2000 |

F I G . 32

| CASSETTE ID | AVAILABLE MEMORY SPACE | AVAILABLE TIME | CUMULATIVE NO OF EVENTS OF IMAGING | DATE OF CORRECTION UPDATING FOR OFFSET CORRECTION | OUTER SIZE | PIXEL NO |
|---|---|---|---|---|---|---|
| DR0002 | 200 MB | 40 MIN | 1,200 | 2015.05.08 10:05 | 17x17 INCHES | 2000×2000 |
| DR0003 | 500 MB | 120 MIN | 2,000 | 2015.05.11 09:00 | 14x17 INCHES | 1600×2000 |
| DR0004 | 20 MB | 20 MIN | 500 | 2015.05.07 16:00 | 17x17 INCHES | 2000×2000 |
| DR0001 | 150 MB | 80 MIN | 800 | 2015.05.11 09:30 | 14x17 INCHES | 1600×2000 |
|  | 2ND STATE INFO | | | | SPECIFICATION INFO | |

| CASSETTE ID | SCORE OF AVAILABLE MEMORY SPACE | SCORE OF AVAILABLE TIME | SCORE OF OUTER SIZE | SCORE OF PIXEL NO | TOTAL SCORE |
|---|---|---|---|---|---|
| DR0002 | 7 | 4 | 10 | 10 | 52 |
| DR0003 | 10 | 10 | 0 | 0 | 31 |
| DR0004 | 1 | 1 | 10 | 10 | 28 |
| DR0001 | 4 | 7 | 0 | 0 | 16 |

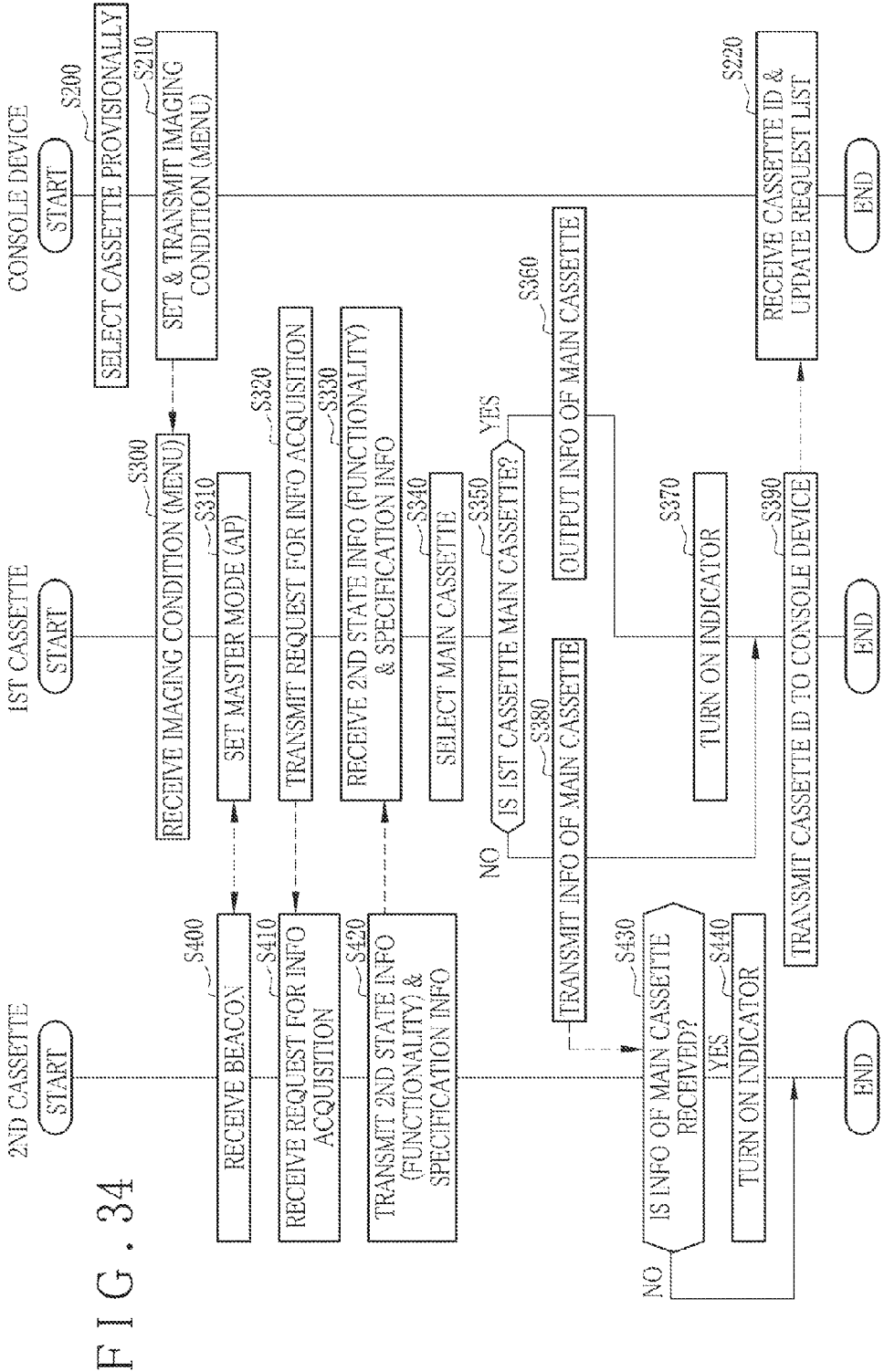

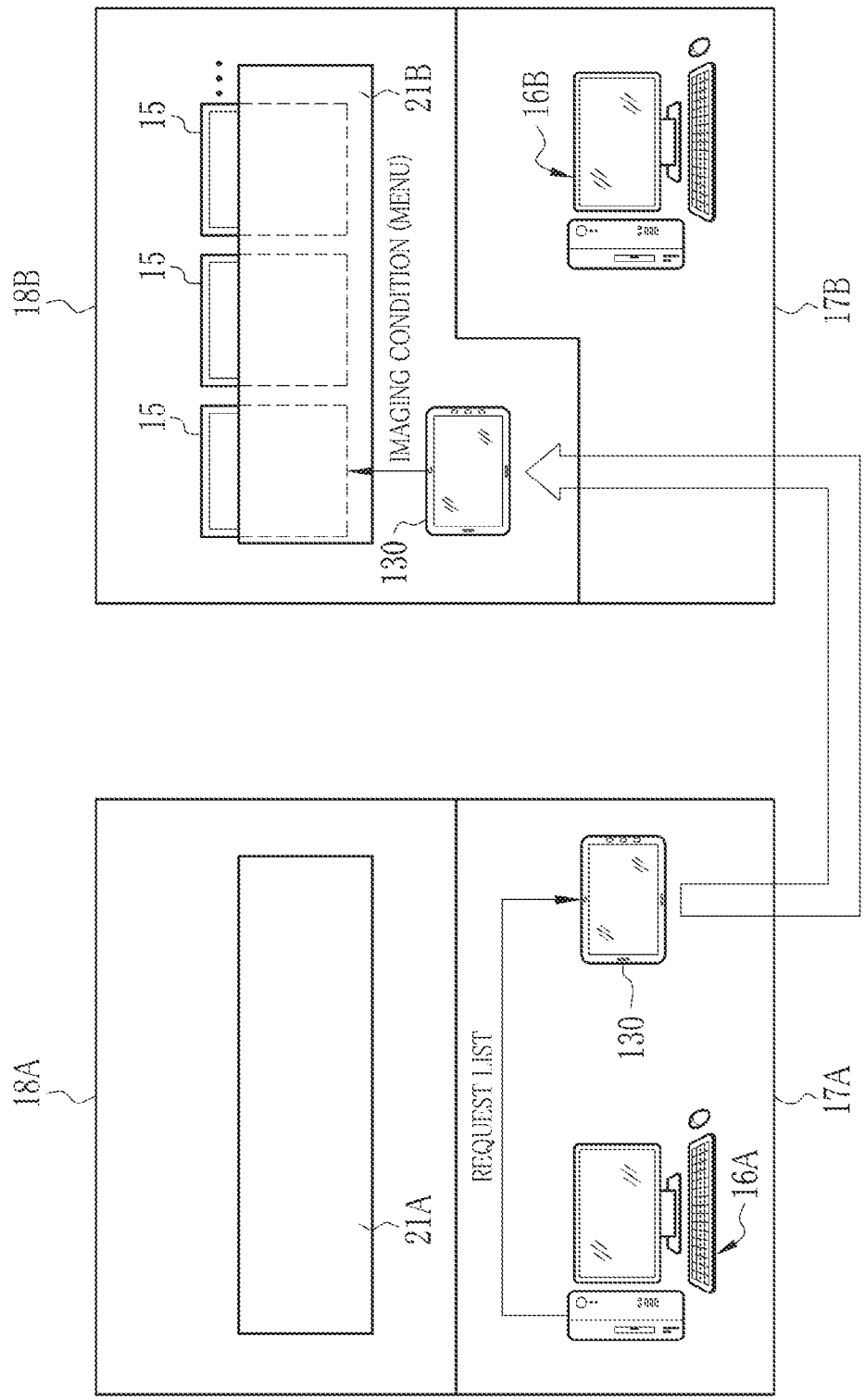

RADIOGRAPHIC IMAGING APPARATUS AND ELECTRONIC CASSETTE

CROSS-REFERENCE TO RELATED APPLICATION

This application claims priority under 35 USC 119 from Japanese Patent Application No. 2015-109583, filed 29 May 2015, the disclosure of which is incorporated by reference herein.

BACKGROUND OF THE INVENTION

1. Field of the Invention

The present invention relates to a radiographic imaging apparatus and electronic cassette. More particularly, the present invention relates to a radiographic imaging apparatus and electronic cassette in which radiographic imaging can be performed continuously and smoothly in a workflow without unwanted interruption.

2. Description Related to the Prior Art

A radiographic imaging apparatus or system, or X-ray imaging apparatus or system is known in the field of the medical diagnosis for imaging of a patient body by use of radiation or X-rays. The radiographic imaging apparatus includes a radiographic imaging device (apparatus) or X-ray imaging device (apparatus), and a console device or user terminal device. The radiographic imaging device detects (generates) a radiation image according to X-rays transmitted through the patient body or object. The console device communicates with the radiographic imaging device for transmitting various data and the radiation image.

A sensor panel or detection panel is incorporated in the radiographic imaging device, for example, a flat panel detector (FPD). Numerous pixels are arranged in the sensor panel and store charge upon receiving X-rays or radiation transmitted through the patient body. The sensor panel reads out the charge stored in the pixels, converts the charge into an image signal, and outputs a radiation image. The radiographic imaging device has the sensor panel, and also a memory and a communication interface. The memory stores the radiation image from the sensor panel in a temporary manner. The communication interface transmits the radiation image to the console device.

Well-known examples of the radiographic imaging device include an installed type and a portable type. The installed type is installed with a floor stand or patient table disposed in an examination room for radiographic imaging. The portable type has a portable housing and the sensor panel contained in the housing. The portable type of the radiographic imaging device is referred to as an electronic cassette for radiographic imaging. The electronic cassette as a mobile device can be carried to various locations in a hospital facility other than the examination room. For example, the electronic cassette is utilized for mobile imaging, namely, for imaging in a patient room for a patient who cannot walk to the examination room. Also, the electronic cassette may be used in various sites external to the hospital facility, for example, in a home of an elderly patient for home care services, in an emergency site of an accident or disaster where injury of a patient should be cared.

For the mobile imaging, a doctor, technician or operator positions the electronic cassette relative to the patient body, for example, sets the electronic cassette between the lying patient body and the bed, makes the patient hold the electronic cassette manually, or the like. Assuming that a cable is physically connected to the electronic cassette for communication with the console device, the cable is likely to obstruct smooth handling of the electronic cassette. In view of this problem, various ideas for wireless connection for the electronic cassette to the console device have been suggested, for example, in JP-A 2013-039322.

JP-A 2013-039322 discloses the radiographic imaging apparatus for radio communication between the electronic cassette and the console device. The disclosure of the document includes a method of preventing erroneous identification of the electronic cassette selected for the radiographic imaging and plural electronic cassettes different from the electronic cassette. For this purpose, the plural electronic cassettes are operated to measure their distances to the console device, by utilizing to strength of radio waves of the radio communication. One of the plural electronic cassettes that is the nearest to the console device is detected by evaluating the measured distances. Assuming that the nearest electronic cassette to the console device is different from the electronic cassette selected for the radiographic imaging, then alarm information is generated to inform the user or operator of possibility of erroneous identification of the electronic cassette.

The electronic cassette disclosed in JP-A 2013-039322 has a function of wirelessly communicating with the plural electronic cassettes located nearby. In the document, the electronic cassette selected for the radiographic imaging communicates with the plural electronic cassettes wirelessly. The plural electronic cassettes generate and transmit distance information to the electronic cassette being selected. The electronic cassette being selected generates and transmits the distance information of the plural electronic cassettes to the console device.

In case the electronic cassette is off-line from the console device in the course of transmitting the radiation image from the electronic cassette to the console device, then the radiation image remains stored in a memory of the electronic cassette until recovery of the communication. Assuming that the memory of the electronic cassette is short of an available memory space sufficient for storing a new radiation image, the radiographic imaging by use of the electronic cassette is impossible until the recovery of the communication. A problem arises in interruption in a workflow of the radiographic imaging. Efficiency in the radiographic imaging is considerably low, as waiting time on a side of the user or operator or the patient becomes long.

SUMMARY OF THE INVENTION

In view of the foregoing problems, an object of the present invention is to provide a radiographic imaging apparatus and electronic cassette in which radiographic imaging can be performed continuously and smoothly in a workflow without unwanted interruption.

In order to achieve the above and other objects and advantages of this invention, a radiographic imaging apparatus includes a console device. A first electronic cassette is connected with the console device communicably, for generating a radiation image of an object by detecting radiation passed through the object, to transmit the radiation image to the console device. A second electronic cassette is connected with the console device communicably, connected wirelessly with the first electronic cassette communicably, for generating a radiation image of an object by detecting radiation passed through the object, to transmit the radiation image to the console device. A mode control unit changes over the first electronic cassette between a normal transmission mode and a relay transmission mode, wherein in the normal transmission mode, the radiation image is transmitted through a path from the first electronic cassette to the console device, and in the relay transmission mode, the radiation image is transmitted from the first electronic cassette to the second electronic cassette wirelessly and then from the second electronic cassette to the console device.

Preferably, the mode control unit, in case the first electronic cassette is in a predetermined specific state, sets the relay transmission mode, and in case the first electronic cassette is in a state different from the specific state, sets the normal transmission mode.

Preferably, the first electronic cassette includes a memory for temporarily storing the radiation image. The specific state is a state of shortage in an available memory space in the memory, or a state of unavailability of the normal transmission mode.

Preferably, the second electronic cassette is constituted by plural second electronic cassettes. The first electronic cassette includes a first data acquisition unit for acquiring first state information of a state of the second electronic cassettes from respectively the plural second electronic cassettes. A cassette selection unit determines a functional cassette among the plural second electronic cassettes according to the first state information for wirelessly transmitting the radiation image in the relay transmission mode.

Preferably, the second electronic cassette includes a memory for temporarily storing the radiation image. The first state information is related to an available memory space in the memory, or connectivity of the second electronic cassette with the console device. The cassette selection unit determines the functional cassette from the second electronic cassette having the available memory space sufficient for storing the radiation image, or which is communicable with the console device in the connectivity.

Preferably, the functional cassette upon receiving the radiation image from the first electronic cassette transmits original sender information to the console device for expressing the first electronic cassette for a sender of the radiation image so as to transmit the radiation image to the console device.

Preferably, the second electronic cassette is operable as an access point, and the access point in the functional cassette transmits the radiation image to the console device.

In another preferred embodiment, the first electronic cassette is operable as an access point, and the access point wirelessly communicates with the second electronic cassette, and receives the first state information.

In one preferred embodiment, the specific state is a state of longitudinal imaging for a continuous region including plural body parts of the object by combining the first and second electronic cassettes.

Preferably, in the state of the longitudinal imaging, the mode control unit sets the relay transmission mode in the first electronic cassette, to transmit the radiation image wirelessly to the second electronic cassette. The radiation images from the first and second electronic cassettes are transmitted together from the second electronic cassette to the console device.

Preferably, in the longitudinal imaging, the first and second electronic cassettes are arranged within an exposure field of radiation, for imaging the object simultaneously.

In still another preferred embodiment, furthermore, a cassette selection unit selects a main cassette for use in the imaging among the first and second electronic cassettes according to comparison of information of the first and second electronic cassettes.

Preferably, the first electronic cassette includes a condition acquisition unit for acquiring an imaging condition determined according to a request for imaging. A data acquisition unit acquires state information of a state of the second electronic cassette. A specification acquisition device acquires specification information of the second electronic cassette. The cassette selection unit operates according to the imaging condition, the state information and the specification information.

Preferably, the second electronic cassette includes a memory for temporarily storing the radiation image. The state information is at least related to an available memory space in the memory and available time of use of a battery for powering the second electronic cassette.

Preferably, each of the first and second electronic cassettes includes an indicator for indicating information of selection of the main cassette in the cassette selection unit.

Also, an electronic cassette, connected with a console device communicably, for generating a radiation image of an object by detecting radiation passed through the object, to transmit the radiation image to the console device, includes a radio communication unit for wirelessly communicating with an external electronic cassette. A mode control unit changes over between a normal transmission mode and a relay transmission mode, wherein in the normal transmission mode, the radiation image is transmitted through a path to the console device, and in the relay transmission mode, the radiation image is transmitted from the radio communication unit to the external electronic cassette and then from the external electronic cassette to the console device.

Consequently, radiographic imaging can be performed continuously and smoothly in a workflow without unwanted interruption, because transmission of a radiation image can be performed reliably by use of an indirect path from the second electronic cassette to the console device even upon occurrence of a technical problem of inefficiency with the direct path to the console device.

BRIEF DESCRIPTION OF THE DRAWINGS

The above objects and advantages of the present invention will become more apparent from the following detailed description when read in connection with the accompanying drawings, in which:

FIG. 3 is a data chart illustrating a request for imaging;

FIG. 4 is a table illustrating data items in a cassette data table;

FIG. 5 is a table illustrating data items in an exposure condition table;

FIG. 6 is a table illustrating a request list;

FIG. 26 is a block diagram schematically illustrating selection of the first electronic cassette as a functional cassette;

FIG. 27 is a block diagram schematically illustrating selection of the second electronic cassette as a functional cassette;

FIG. 28 is a block diagram schematically illustrating the controller;

FIG. 29 is a data chart illustrating the second state information;

FIG. 30 is a data chart illustrating the specification information;

FIG. 31 is a data chart illustrating recommended specification information;

FIG. 32 is a table illustrating a second information list;

FIG. 33 is a table illustrating a score list;

FIG. 34 is a flow chart illustrating operation of the fourth preferred embodiment;

FIG. 35 is a block diagram schematically illustrating use of portable information terminal equipment.

DETAILED DESCRIPTION OF THE PREFERRED EMBODIMENT(S) OF THE PRESENT INVENTION

First Embodiment

Figure 1:
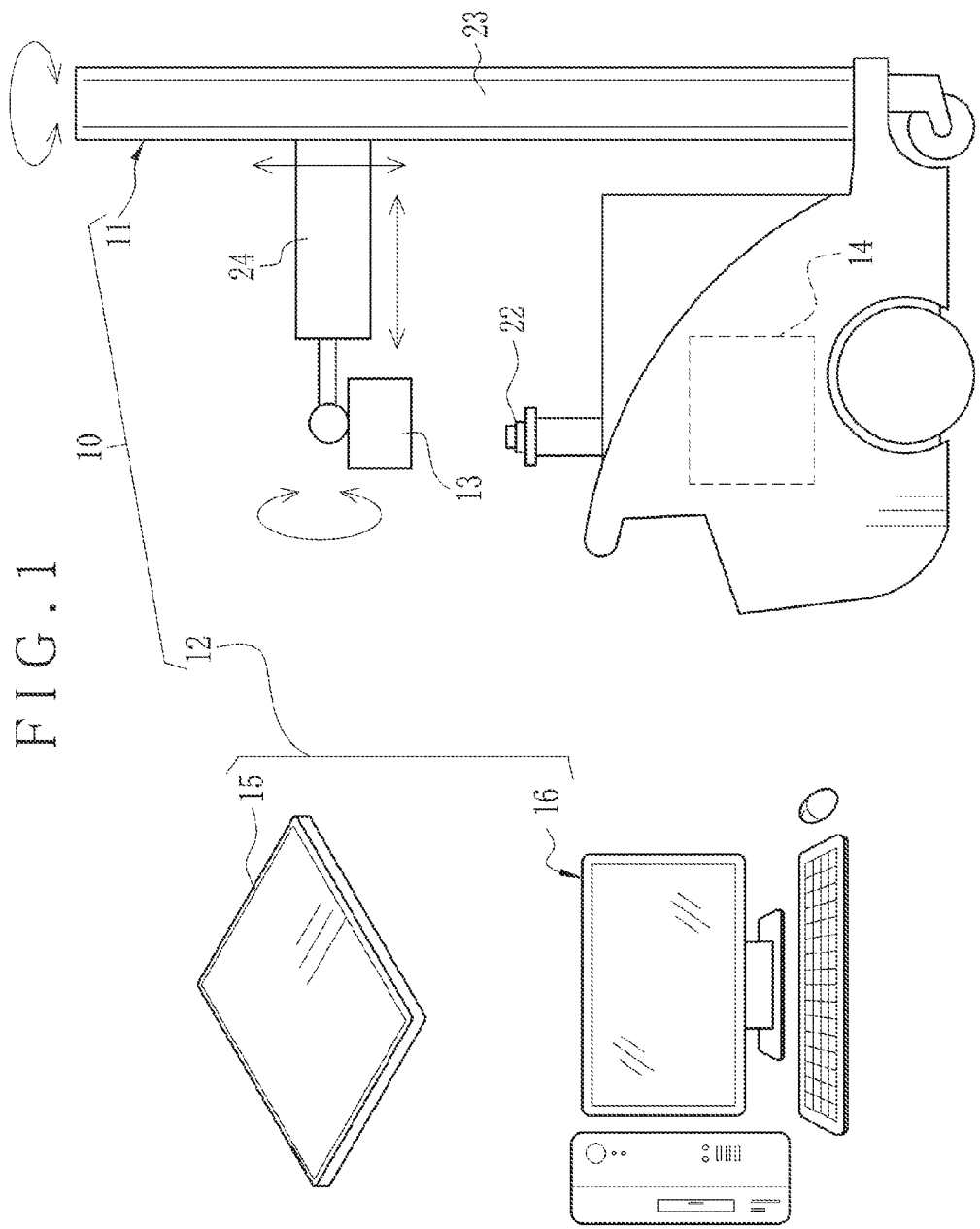
FIG. 1 is an explanatory view in a side elevation illustrating a radiographic imaging system.
Figure 2:
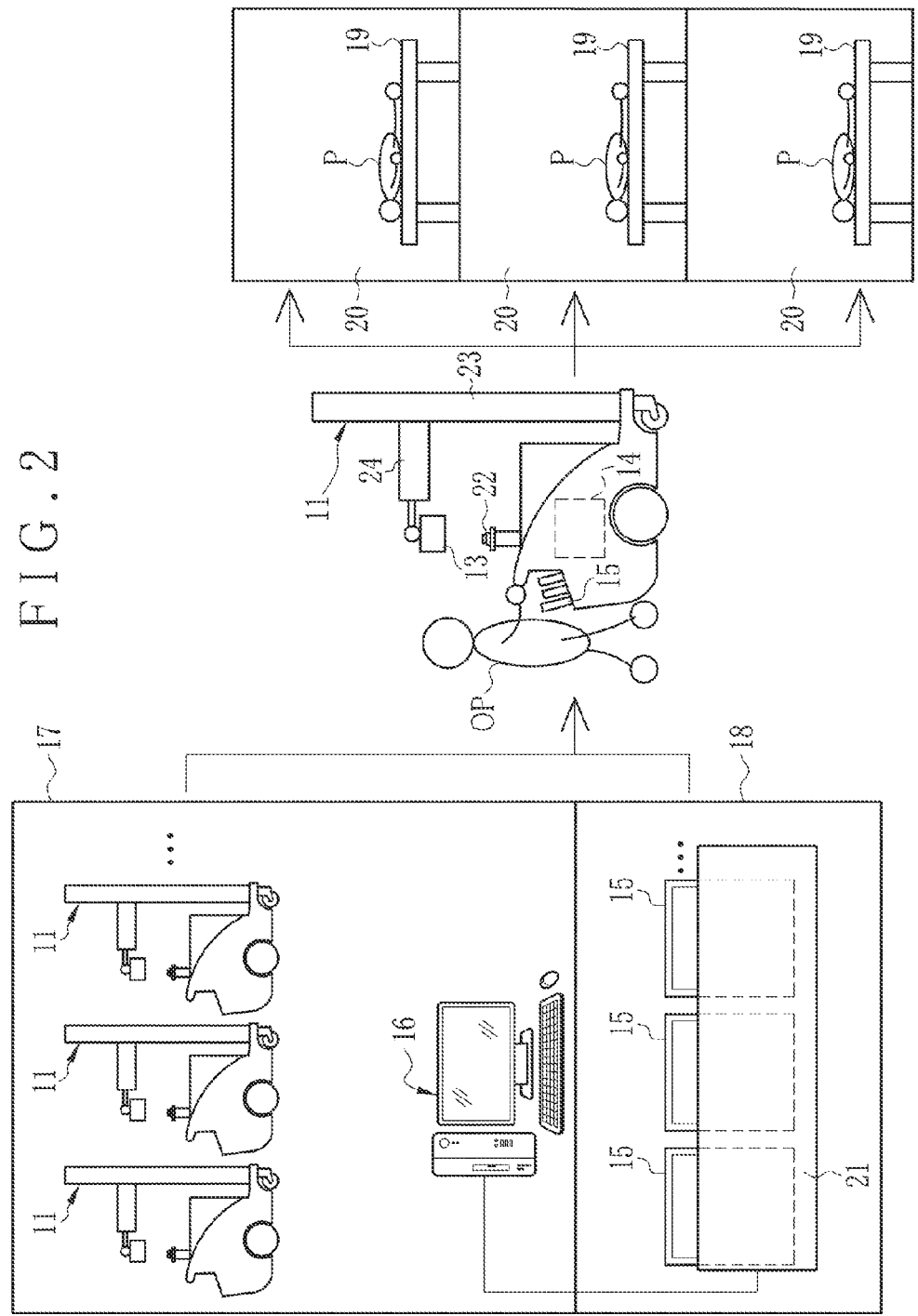
FIG. 2 is an explanatory view in a side elevation illustrating mobile imaging.

In FIGS. 1 and 2, a radiographic imaging system 10 or X-ray imaging system includes a medical cart 11 (radiation generator) for radiology, and a radiographic imaging apparatus 12 or X-ray imaging apparatus. The medical cart 11 includes a radiation source 13 or X-ray source and a source control unit 14. The radiographic imaging apparatus 12 includes an electronic cassette 15 for radiographic imaging, and a console device 16 or user terminal device.

The medical cart 11 is a mobile device including a housing, cart wheels and the radiation source 13 and the source control unit 14 disposed in the housing. The term of the medical cart 11 is to refer to the housing and its relevant elements.

The radiology department in the hospital facility includes a storage room 17 or preparation room, where the medical cart 11 is placed while not used. The medical cart 11 is moved from one of patient rooms 20 to another for mobile imaging or radiographic imaging. At first, an operator OP or doctor or radiologist (radiology technician) moves out the medical cart 11 from the storage room 17, for positioning in the patient room 20. A patient P is disposed in each of the patient rooms 20 on a bed 19. He or she is bedridden and cannot walk to an examination room 18 disposed next to the storage room 17.

A plurality of the electronic cassettes 15 are prepared. A cradle unit 21 or charging cradle is installed in the examination room 18, and stores the electronic cassettes 15 while the electronic cassettes 15 are not used. For example, a plurality of receiving slots are formed in the cradle unit 21 for positioning respectively the electronic cassettes 15, so as to charge the electronic cassettes 15 electrically.

The cradle unit 21 is connected to the console device 16 in a wired manner. While the electronic cassette 15 is stored in the cradle unit 21 in the examination room 18, the electronic cassette 15 is set communicable with the console device 16 by the cradle unit 21.

The electronic cassette 15 is taken out by the operator OP from the cradle unit 21 for use in X-ray imaging. For the purpose of mobile imaging, the electronic cassette 15 is moved from the examination room 18 to the storage room 17, carried on the medical cart 11, and transported from the storage room 17 with the medical cart 11.

The console device 16 can be portable and can be carried on the medical cart 11 for mobile imaging by use of the electronic cassette 15. However, the console device 16 in the embodiment is installed for use in the storage room 17. The electronic cassette 15 has a function for the mobile imaging without changing a location of the console device 16. Moving only the electronic cassette 15 makes it possible to construct a workflow of the mobile imaging in a manner similar to the imaging with the film cassette, IP cassette (imaging plate cassette), CR cassette (computed radiography cassette) or the like well-known in the art.

The radiation source 13 includes an X-ray tube and a collimator. The X-ray tube emits X-rays. The collimator or a field limiting device limits an exposure field of exposure of the X-rays to the patient P. The source control unit 14 controls a tube voltage and tube current for the X-ray tube, and exposure time of the X-rays. A storage area in the source control unit stores a plurality of exposure conditions according to respective body parts, such as a chest and abdomen, the exposure conditions including the tube voltage, tube current and exposure time. A desired one of the exposure conditions are selected and entered by an input of the operator OP.

A radiation switch 22 is manually operated by the operator OP for starting irradiation of X-rays. The radiation switch 22 is a two-step type. In case the radiation switch 22 is depressed halfway at a first depth (step), the source control unit 14 causes the radiation source 13 to perform preparation for irradiation of X-rays. In case the radiation switch 22 is depressed fully at a second depth, the source control unit 14 starts the radiation source 13 to emit X-rays. A timer is incorporated in the source control unit 14 for starting measuring time upon the start of the irradiation. Assuming that the measured time becomes equal to a preset exposure time according to the exposure condition, the radiation source 13 is stopped from emitting X-rays.

The medical cart 11 has a support column 23 and a holder arm 24. The support column 23 extends vertically. The holder arm 24 is disposed on the support column 23 and extends horizontally. The radiation source 13 is disposed at one end of the holder arm 24. The support column 23 is rotatable about an axis extending vertically. The holder arm 24 and the radiation source 13 are rotated by rotation of the support column 23. The holder arm 24 is extendable from the support column 23 and movable up and down. The radiation source 13 is rotatable on the holder arm 24. A position and direction of the radiation source 13 are adjusted by rotation of the support column 23, extension and movement of the holder arm 24 and rotation of the radiation source 13 itself. Lock mechanisms (not shown) are disposed on the support column 23 and the holder arm 24 to lock the support column 23, the holder arm 24 and the radiation source 13 without incidental shift while the medical cart 11 is moved.

The console device 16 receives an input of an imaging request for instructing the operator OP to perform the imaging. The request is input to the console device 16 by the RIS (Radiology Information System) which is not shown.

In FIG. 3, the information of the request for imaging includes data items of a request ID (identification data), case ID, body part, posture, imaging direction, necessity and unnecessity of mobile imaging, and the like. The request ID is alphanumeric information or signs for identifying each request for imaging, and allocated by the RIS automatically. A case ID of the patient P to be imaged is registered in the data item of the case ID. The case ID is alphanumeric information or signs for identifying each patient P.

Information of the body part, posture and imaging direction designated by a doctor having issued the request for imaging is recorded in data items of the body part, posture and imaging direction. Examples of the body parts are a head, cervical spine, chest, abdomen, hands, fingers, elbows, knees and the like. Examples of the postures of the patient P are a standing posture, lying posture, sitting posture and the like. Examples of the imaging directions of the patient P are an anteroposterior direction (AP), lateromedial direction, posteroanterior direction (PA) and the like.

For a data item of requirement of the mobile imaging, information related to the patient P for necessity or unnecessity of the mobile imaging is recorded. Furthermore, data items of personal information are included in the imaging request, such as a name, sex, age, height and weight of the patient P. It is additionally possible to provide other data items associated with the imaging request, such as information of a hospital department or doctor as a requester of the imaging request, a data and time of receiving the imaging request in the RIS, purposes for imaging, a message from the doctor to a radiologist, or the like. The purposes include observation of a progress after the surgery, observation of effect of a drug for treatment, and the like.

In FIG. 4, a cassette data table 30 is stored in the console device 16, and includes registered data of combinations of cassette IDs of the plural electronic cassettes 15, and their names, outer sizes and the like. At most five electronic cassettes 15 can be registered in the cassette data table 30. The names are information of the electronic cassettes 15 determined by naming of the operator OP.

The plural electronic cassettes 15 include those of two or more types different from one another. An equal type of the cassette is a cassette having the same outer size and same performance. A different type of the cassette is a cassette having a different outer size and/or different performance. For example, "A cassette" with a cassette ID of DR0001 is the same type as "C cassette" with a cassette ID of DR0003, because of the equal outer size of 14×17 inches and the same performance. "B cassette" with a cassette ID of DR0002 and "D cassette" with a cassette ID of DR0004 are a different type from "A cassette" and "C cassette", because of their outer size of 17×17 inches.

In FIG. 5, an exposure condition table 32 is stored in the console device 16. The exposure condition table 32 contains registered data of an imaging condition (menu for the object) and exposure condition associated therewith. The imaging condition is a set of a body part in a patient body, posture of the patient body, and imaging direction. Note that an imaging condition according to the embodiment can include the body part and imaging direction without including the posture, or can be a special imaging condition (menu for the object) corresponding to a tomosynthesis imaging or other special imaging.

The console device 16 is operated by the operator OP to cause a display panel to display a request list in which requests for imaging in FIG. 3 are listed. The operator OP views the request list and checks the requests. The display panel displays a selection window in which plural electronic cassettes 15 are indicated as registered in the cassette data table 30. The operator OP selects the electronic cassette 15 for use in the imaging for the respective requests among the plural electronic cassettes 15 in the selection window.

Then the console device 16 drives the display panel to display the information in the exposure condition table 32 in a form with a settable imaging condition (menu for the object). The operator OP selects one of the imaging conditions for coincidence in the body part, posture and imaging direction designated by the request for imaging. The console device 16 transmits the request ID, the console ID, the selected imaging condition and the exposure condition to the electronic cassette 15, the console ID being alphanumeric expressions or signs for identification, the selected imaging condition being set by the operator OP.

The console device 16 provides an image file of the radiation image in a form according to the standards of the DICOM (Digital Imaging and Communication in Medicine), and transmits the image file to the PACS (Picture Archiving and Communication System) which is not shown. The image file includes various data portions, such as the radiation image, a request ID, cassette ID, personal information, imaging condition (menu for the object), exposure condition and other meta information, which are associated together by use of one image ID. A doctor of a hospital department after issuing the imaging request is enabled to download the image file by access to the PACS from a terminal device in the hospital department, so as to view the radiation image.

In FIG. 6, a request list 35 is produced by the console device 16. The request list 35 contains a case ID, room number of the patient room 20, requirement of mobile imaging, cassette ID, imaging condition (menu for the object), exposure condition and image ID, in association with the request ID of each of the requests for imaging. The case ID is for the patient P of interest. The cassette ID is for the electronic cassette 15 selected for use by the operator OP. The imaging condition is determined by the operator OP. The exposure condition corresponds to the imaging condition. The image ID is for a radiation image corresponding to the request.

For a data item of the image ID, an image ID is registered upon receiving a radiation image from the electronic cassette 15 of the cassette ID registered in the data item of the cassette ID. While no radiation image is received from the electronic cassette 15, no image ID is registered in the data item of the image ID, so that the data item is blank.

The information in the request list 35 can be printed on a paper material in relation to the console device 16. Registered data (not shown) in the request list 35 includes personal information of the patient P in the request for imaging, the name of the electronic cassette 15, and operator information of the operator OP. The personal information includes a name, sex, age, height, weight and the like of the patient P. The operator information includes an ID, name and the like of the operator OP.

Only one request for imaging can be issued for one patient P. Sometimes a plurality of requests for imaging may be issued simultaneously for one patient P. For this situation, recognition information is added to the request IDs of the plural requests for imaging, to express the association with the single patient P, such as request IDs of OD0001-A, OD0001-B for the case ID of P0050 of the patient P.

Figure 7:
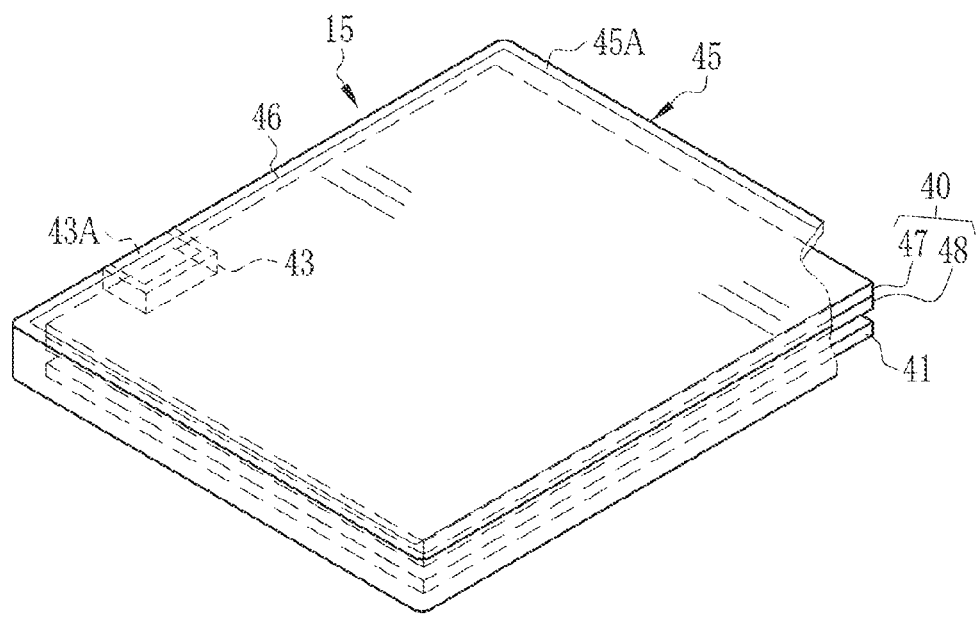
FIG. 7 is a perspective view illustrating an electronic cassette.
Figure 8:
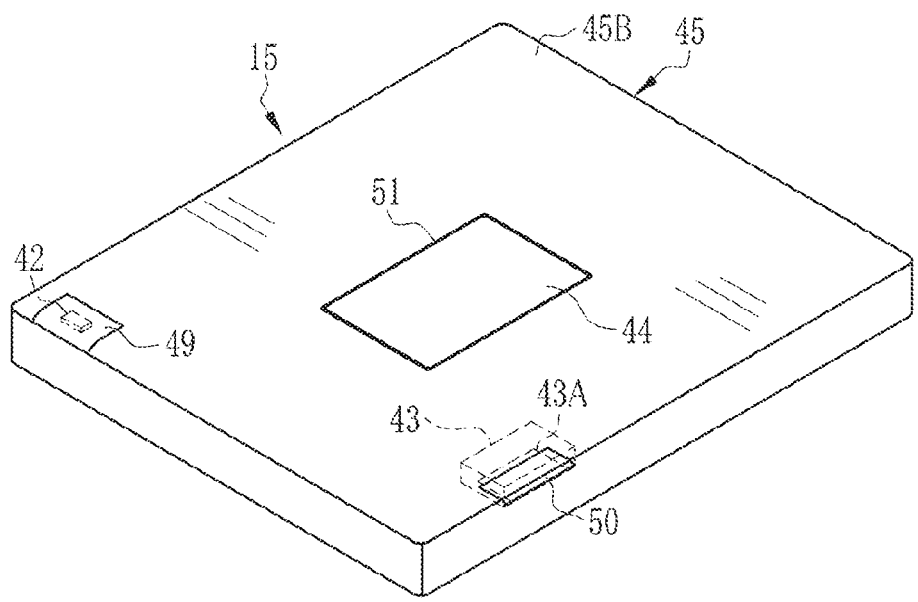
FIG. 8 is a rear perspective view illustrating the electronic cassette.

In FIGS. 7 and 8, the electronic cassette 15 includes a sensor panel 40 or detection panel, a circuit board 41, a radio communication unit 42 (radio communication interface) for an access point node (AP), a wired communication interface 43, a battery 44 and a portable housing 45, which contains those elements and has a quadrilateral form.

The portable housing 45 has a size according to the International Standards ISO (International Organization for Standardization) 4090:2001 in the same form as a film cassette, IP cassette, CR cassette and the like. The portable housing 45 has a quadrilateral opening formed in a front surface 45A, and a radio transparent plate 46 fitted in the quadrilateral opening. The electronic cassette 15 is so positioned as to direct the radiation source 13 to the front surface 45A. Also, various elements (not shown) are included in the portable housing 45, such as a switch for turning on and off a main power source, an indicator for informing an operation state of the electronic cassette 15, for example, available time of use of the battery 44, a state of readiness for imaging, and the like.

The sensor panel 40 includes a scintillator 47 and a photosensitive plate 48. The scintillator 47 and the photosensitive plate 48 are arranged in a direction toward the rear with reference to the front surface 45A where the X-rays are incident. The scintillator 47 contains phosphor CsI:Tl (thallium activated cesium iodide), $Gd_2O_2S$:Tb or GOS (terbium activated gadolinium oxysulfide), and the like, and converts incident X-rays through the radio transparent plate 46 into visible light for emission of the light. Note that a sensor panel can be so structured that the photosensitive plate 48 and the scintillator 47 are arranged in the direction toward the rear with reference to the front surface 45A. Also, a sensor panel can be a direct converting type for converting X-rays into signal charge directly by use of amorphous selenium as a photoconductive layer.

The photosensitive plate 48 detects visible light from the scintillator 47 and converts the same into an image signal. The circuit board 41 controls the operation of the photosensitive plate 48, and produces a radiation image according to the image signal output by the photosensitive plate 48.

A cover 49 covers the radio communication unit 42, and is formed from electrically non-conductive material having property for transmitting radio waves, for example, resin. The electronic cassette 15 is driven by power from the battery 44 while the radio communication unit 42 is used, and thus can be used in a cableless form.

The wired communication interface 43 performs wired communication with the console device 16. A female connector 43A is provided in the wired communication interface 43. A male connector at a tip of a cable from the console device 16 is connectable with the female connector 43A. A male connector disposed in a receiving slot of the cradle unit 21 is connectable with the female connector 43A. A connector cover 50 covers and protects the female connector 43A while the radio communication is performed, or while no male connector is used.

The electronic cassette 15 is supplied with power through the wired communication interface 43. Connecting the male connector with the female connector 43A powers the electronic cassette 15 with power received from the wired communication interface 43. Also, the battery 44 is charged by the power received from the wired communication interface 43.

The battery 44 is constituted by a secondary cell of a rechargeable structure. The battery 44 supplies various elements in the electronic cassette 15 with power. A rear surface 45B of the portable housing 45 is opposite to the front surface 45A. A battery holder 51 is disposed at the center of the rear surface 45B, and holds the battery 44 in a removable manner, as illustrated in FIG. 8. Also, a positioning mechanism (not shown) is disposed with the battery holder 51 for preventing the battery 44 from dropping out of the battery holder 51 and for releasing the battery 44 from the stopped state, such as a locking/unlocking mechanism.

Figure 9:
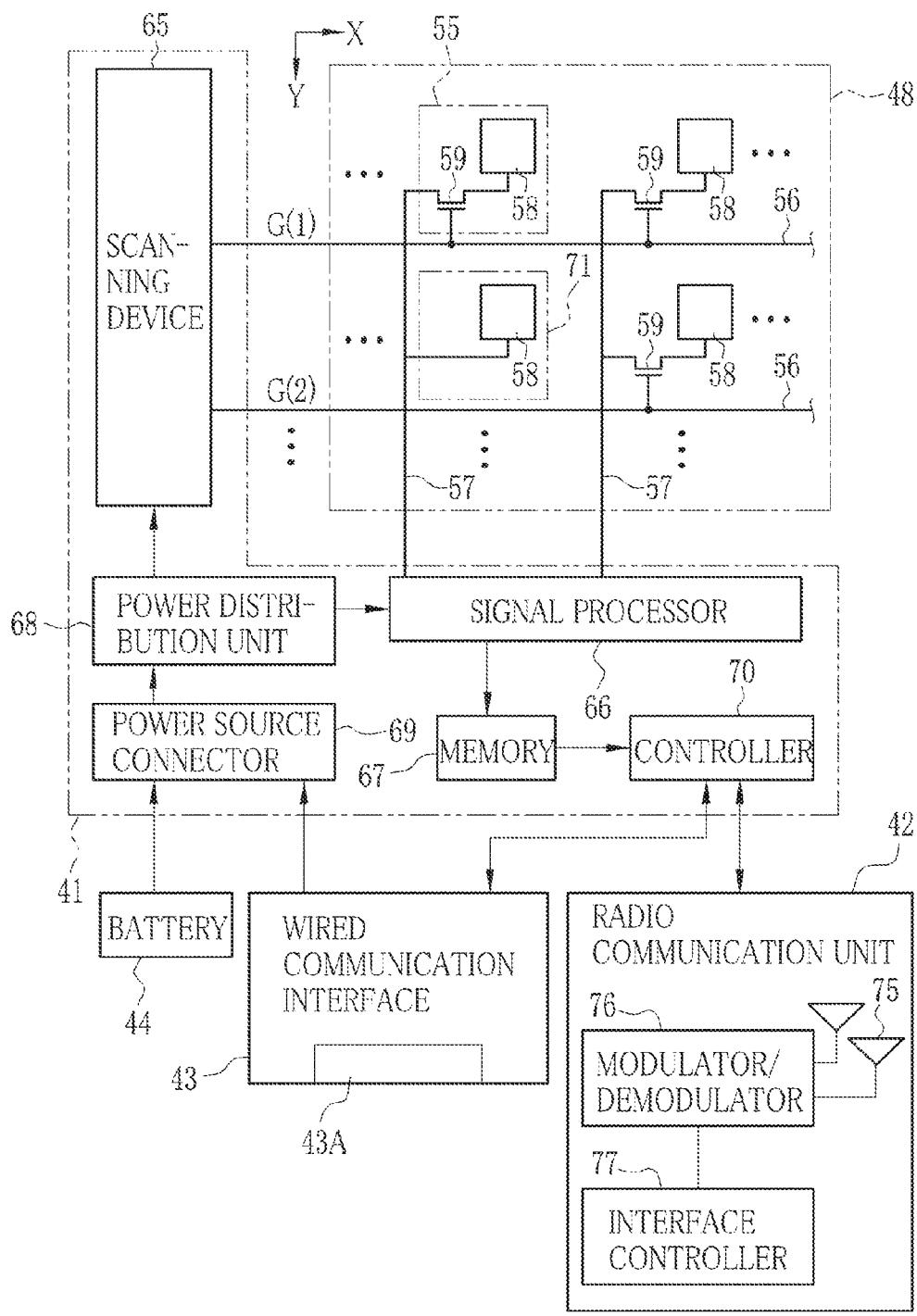
FIG. 9 is a block diagram schematically illustrating the electronic cassette.

In FIG. 9, the photosensitive plate 48 includes numerous pixels 55, N scan lines 56 and M signal lines 57. The pixels 55 are arranged in a matrix form of N×M on a substrate of glass (not shown). The scan lines 56 extend in an X direction along the arrays of the pixels 55, and are arranged at a predetermined pitch in a Y direction along the columns of the pixels 55. The signal lines 57 extend in the Y direction, and are arranged at a predetermined pitch in the X direction. The scan lines 56 are perpendicular with the signal lines 57. The pixels 55 are disposed at intersection points between the scan lines 56 and the signal lines 57. Note that N and M are integers equal to or more than 2, for example, are approximately 2,000. Also, the pixels 55 can be arranged in a honeycomb arrangement in place of a square arrangement of the present embodiment.

Each of the pixels 55 includes a photoconductor 58 for photoelectric conversion and a thin film transistor 59 or TFT. The photoconductor 58 generates charge (electron-hole pair) upon receiving visible light and stores the charge. The thin film transistor 59 is a switching element. The photoconductor 58 includes semiconductor layers for generating the charge, and upper and lower electrodes disposed on the semiconductor layers. An example of the semiconductor layers is a PIN type (p-intrinsic-n), in which an N layer is formed on the side of the upper electrode, and a P layer is formed on the side of the lower electrode. The thin film transistor 59 has a gate connected with the scan lines 56, a source connected with the signal lines 57, and a drain connected with the lower electrode of the photoconductor 58. Also, it is possible to use a sensor panel of CMOS type (Complementary Metal Oxide Semiconductor) instead of the TFT.

A bias line (not shown) is connected to the upper electrode of the photoconductor 58. A bias voltage of a positive value is applied to the upper electrode of the photoconductor 58 by use of the bias line. As an electric field is created in the semiconductor layers by application of the positive bias voltage, the electron in the electron-hole pair generated in the semiconductor layers by photoelectric conversion is moved to the upper electrode and absorbed in the bias line.

The hole in the electron-hole pair is moved to the lower electrode and collected as charge.

The circuit board 41 includes a scanning device 65, a signal processor 66, a memory 67, a power distribution unit 68 or driver, a power source connector 69 and a controller 70.

The scanning device 65 is connected to respective ends of the scan lines 56, and generates a gate pulse G(K) for driving the thin film transistor 59, where K is an integer from 1 to N. The controller 70 drives the thin film transistor 59 by use of the scanning device 65, and causes the sensor panel 40 to operate for pixel reset, storing and image readout. In the pixel reset, dark current is read out from the pixels 55 and reset. In the storing, the charge according to the dose of the X-rays is stored in the pixels 55. In the image readout, charge is read out from the pixels 55.

In the pixel reset and image readout, the scanning device 65 supplies the scan lines 56 with the gate pulse G(K), so that the thin film transistors 59 connected with the scan lines 56 are turned on successively one array after another. In the storing, no gate pulse G(K) is output by the scanning device 65. The thin film transistors 59 are turned off.

The signal processor 66 reads out charge from the pixels 55 and converts this into a digital image signal, which is output to the memory 67. The memory 67 has capacity for storing at least one frame of the radiation image.

The power distribution unit 68 supplies the scanning device 65 with the gate pulse G(K). The power distribution unit 68 supplies the signal processor 66 with a drive voltage. Also, the power distribution unit 68 supplies various circuit devices other than the scanning device 65 and the signal processor 66 with the drive voltage, such as the radio communication unit 42, the memory 67 and the controller 70.

The battery 44 is connected with the power source connector 69. The power source connector 69 is used for supplying various elements in the electronic cassette 15 with power from the battery 44, such as the power distribution unit 68. Also, the wired communication interface 43 is connected with the power source connector 69. In case a male connector is coupled with the female connector 43A in the wired communication interface 43, the power source connector 69 is supplied with power by the wired communication interface 43, so as to power the various elements.

The controller 70 outputs the radiation image in the memory 67 to the radio communication unit 42 or the wired communication interface 43. The controller 70 receives various data from the console device 16 as input by use of the wired communication interface 43, and performs control according to the various data. For example, the controller 70 receives an exposure condition, and changes a processing condition in the signal processor 66 according to the exposure condition. The controller 70 receives a console ID among the various data, and specifies a recipient of the radiation image according to the console ID.

Plural monitor sensors 71 for radiation or X-rays are disposed in the photosensitive plate 48 for detecting a start of irradiation of X-rays. The monitor sensors 71 are arranged in a discrete manner within the entire surface of the photosensitive plate 48.

The monitor sensors 71 are a structure of partial use of the pixels 55. The monitor sensors 71 include the photoconductor 58 in the same manner as the pixels 55, but do not have the thin film transistor 59. The photoconductor 58 in the monitor sensors 71 is directly connected to the signal lines 57. Charge generated by the photoconductor 58 in the monitor sensors 71 is drawn to the signal lines 57 irrespective of a turn-on or turn-off state of the thin film transistor 59.

The charge generated by the photoconductor 58 in the monitor sensors 71 is converted by the signal processor 66 into an image signal and written to the memory 67, in the same manner as the charge generated by the photoconductor 58 in the pixels 55. Note that a term of a dose signal is used herein to express the image signal according to the charge generated by the photoconductor 58 in the monitor sensors 71.

The dose signal is read out repeatedly at a predetermined interval. The dose signal obtained by the readout of one time corresponds to dose of incident X-rays per unit time. After irradiation of X-rays is started, the dose of the incident X-rays per unit time gradually increases, so that the dose signal also increases.

The controller 70 reads out the dose signal from the memory 67 at each time that the dose signal is written to the memory 67, and compares a value of the dose signal with the value of a predetermined detection threshold for detecting a start of the irradiation. The controller 70 judges that the irradiation of X-rays is started upon reach of the dose signal to the detection threshold. Thus, the start of the irradiation can be detected in the electronic cassette 15 without receiving a sync signal expressing the start of the irradiation from the source control unit 14.

As the dose signal can be read out even during the storing of the sensor panel 40, it is possible to detect an end of the irradiation of X-rays in the controller 70 by comparison of the dose signal with a predetermined detection threshold for the end of the irradiation.

The controller 70 upon receiving the imaging condition (menu for the object) and the exposure condition from the console device 16 causes the sensor panel 40 to start reading out the dose signal. Upon detecting the start of the irradiation, the controller 70 causes the sensor panel 40 to perform the pixel reset, and then perform the storing. Even after the start of the storing, the controller 70 causes the sensor panel 40 to continue reading out the dose signal. The controller 70 detects completion of the irradiation in case the dose signal becomes equal to or less than the detection threshold. The controller 70 completes the storing upon detecting the completion of the irradiation. The controller 70 causes the sensor panel 40 to perform the image readout.

The radio communication unit 42 includes a communication antenna 75, a modulator/demodulator 76 and an interface controller 77 (transmission controller). The modulator/demodulator 76 performs modulation of data by combining the data with a carrier or wave, and performs demodulation to retrieve the data from the carrier received by the antenna 75. The interface controller 77 controls the transmission according to the standards of the wireless LAN (Local Area Network). Specifically, the interface controller 77 operates according to a communication protocol of TCP/IP (Transmission Control Protocol/Internet Protocol), or according to a communication protocol of IEEE 802.11n (IEEE being the Institute of Electrical and Electronics Engineers, Inc.).

The communication protocols are in plural layers according to the reference model of the Open Systems Interconnection (OSI). The communication is performed by a combined use of a plurality of communication protocols with a difference in the layer. TCP/IP is a communication protocol used also for the wired LAN, and used as a higher layer in the wireless LAN. IEEE 802.11n is a communication protocol in a layer directly lower than the TCP/IP, and determines a process of the communication of a wireless form.

There is no cable connected physically in the radio communication unlike the wired communication. The radio communication unit 42 in the electronic cassette 15 is required to perform logical connection with other wireless terminal device, such as the electronic cassette 15 and the console device 16. The radio communication unit 42 is operable in a master mode (parent device mode) and a slave mode (child device mode) for the radio communication with the wireless terminal device. The master mode is for operation as an access point (AP). The slave mode is for radio communication with another wireless terminal device by cooperation of an access point being discrete from the radio communication unit 42. The interface controller 77 changes over between the master and slave modes.

For the radio communication between the wireless terminal devices, normally an access point discrete from the wireless terminal devices is used. However, the radio communication unit 42 of the electronic cassette 15 is used as the access point in the embodiment. The radio communication between the electronic cassettes 15 as the wireless terminal devices can be performed without using an access point discrete from the wireless terminal devices.

Figure 10:
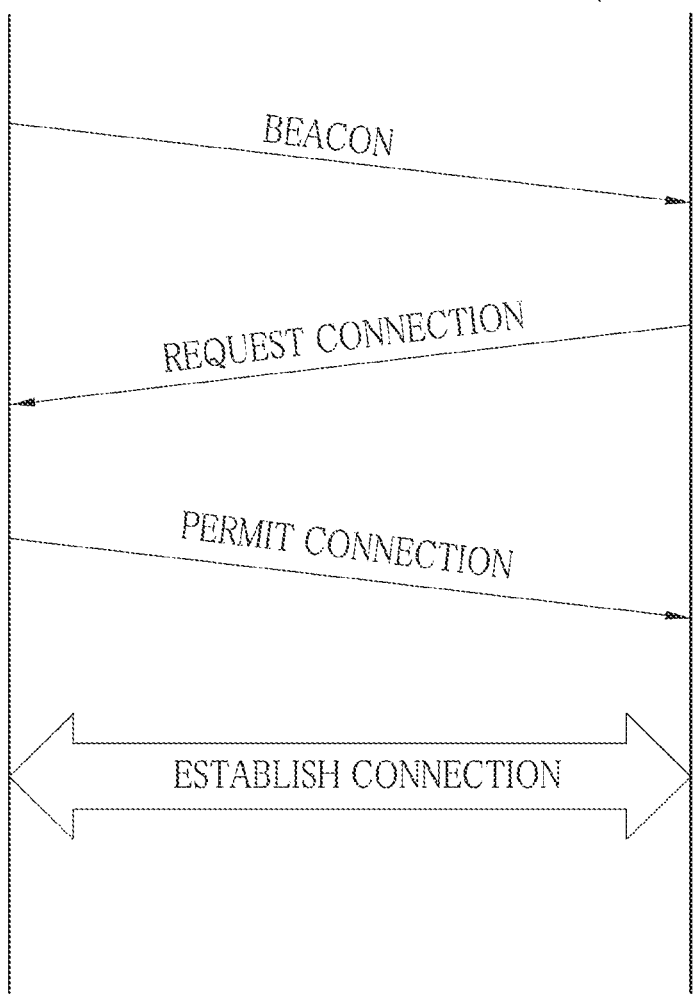
FIG. 10 is a timing chart illustrating a connecting sequence of the electronic cassette.

Steps of connection and communication are described by referring to FIG. 10 in a form defined by IEEE 802.11n between the electronic cassette 15 and the wireless terminal device while the radio communication unit 42 operates in the master mode. The wireless terminal device has a second radio communication unit of a construction similar to the radio communication unit 42. Let the second radio communication unit operate in the slave mode.

The radio communication unit 42, operating as the access point in the master mode in FIG. 10, emits a beacon or radio waves at a predetermined interval as long as 100 msec. The beacon is a signal for expressing presence of the electronic cassette 15 to wireless terminal devices present around the electronic cassette 15. The wireless terminal devices monitor reception of the beacon always by use of the radio communication unit in the course of an active state. The wireless terminal devices can receive the beacon while located in the area of the reach of the beacon. The area of the reach is a circular area with a radius of 5 meters around the radio communication unit 42.

Data in the beacon includes a network identifier, such as SSID (Service Set Identifier) and ESSID (Extended Service Set Identifier). The network identifier is specific information allocated to the access point of the radio communication unit 42, a network having the access point, or the like, for recognition from the wireless terminal devices.

The network identifier of the radio communication unit 42 is registered in the second radio communication unit of the wireless terminal device. The second radio communication unit upon receiving the beacon having the predetermined network identifier generates a request for connection. The radio communication unit 42 receives the request for connection, and performs verification for the wireless terminal device as a requester of the request. For this purpose, the second radio communication unit transmits the request inclusive of verification information, such as a password.

The radio communication unit 42 upon receiving the connection request performs verification by checking the received password and a predetermined password, and transmits information of allowance to the wireless terminal device assuming that the password is verified. A logical communication link is established between the electronic cassette 15 and the wireless terminal device upon receiving the information of the allowance, to connect the wireless terminal device to the electronic cassette 15 remotely.

In FIG. 10, only one wireless terminal device is illustrated. However, all of the plural wireless terminal devices present in the area of the reach of the beacon perform the connecting sequence in cooperation with the electronic cassette 15. The radio communication between the electronic cassette 15 and the plural wireless terminal devices is enabled by the relay of the radio communication unit 42 operating as the access point.

In case the radio communication unit 42 is operated in the slave mode, the basic connecting sequence is equally used, by reading an access point discrete from the electronic cassette 15 in place of "electronic cassette" in FIG. 10 and reading the electronic cassette 15 and wireless terminal device in place of the "wireless terminal device". The radio communication between the electronic cassette 15 and the wireless terminal device is possible by cooperation of relay of the access point discrete from the electronic cassette 15, in the same manner as the radio communication unit 42 operating in the master mode.

In the operation of the master mode, the radio communication unit 42 continues emitting the beacon even after establishing the connection with the wireless terminal device. The connection between the electronic cassette 15 and the wireless terminal device is continued while the beacon is received, but terminated upon termination of receiving the beacon at the wireless terminal device. Examples of the termination of the reception are stop of emission of the beacon from the radio communication unit 42, shift of the wireless terminal device out of the area of the reach of the beacon, and the like. In case the wireless terminal device enters the area of the reach of the beacon again, the connecting sequence described above is performed again for reconnection, because the reception of the beacon to the wireless terminal device is enabled.

In the embodiment, one of the plural electronic cassettes 15 carried on the medical cart 11 in the mobile imaging becomes the electronic cassette 15 operating in the master mode in FIG. 10. All of the remainder in the plural electronic cassettes 15 become wireless terminal devices operating in the slave mode. Thus, the radio communication is possible between the plural electronic cassettes 15.

Figure 11:
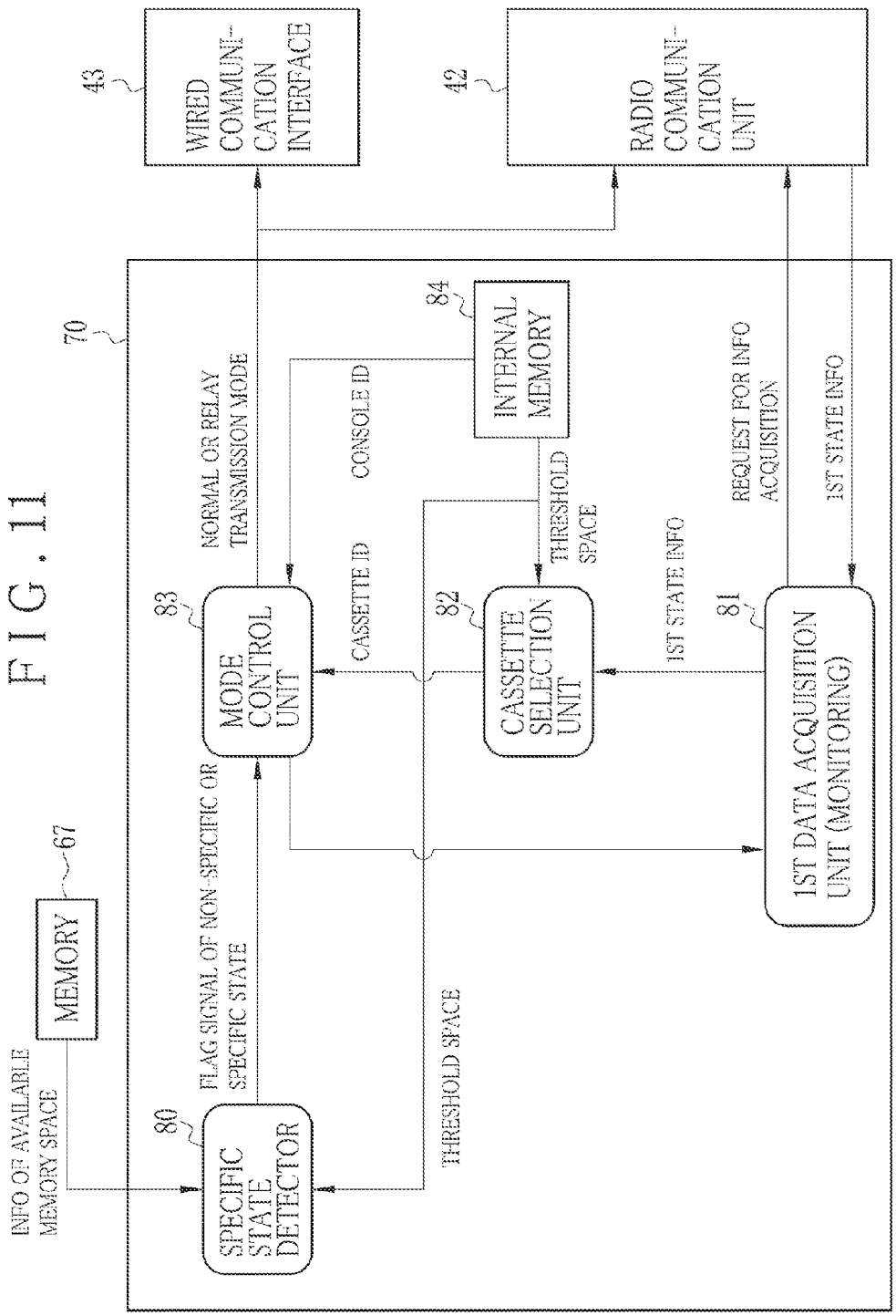
FIG. 11 is a block diagram schematically illustrating a controller.

In FIG. 11, the controller 70 in the electronic cassette 15 in the operation includes a specific state detector 80, a first data acquisition unit 81 for state information (for monitoring functionality), a cassette selection unit 82 and a mode control unit 83. The specific state detector 80 checks whether or not the electronic cassette 15 is in a predetermined specific state (functionality). In the embodiment, the specific state is a state of short of a memory space required for storing one frame of a radiation image in the memory 67.

The first data acquisition unit 81 acquires the first state information from a second electronic cassette 15B for radiographic imaging. In the embodiment, the first state information is information of an available memory space of the memory 67 of the second electronic cassette 15B.

The cassette selection unit 82 determines a functional cassette or the second electronic cassette 15B for wirelessly transmitting the radiation image in the relay transmission mode to be described later according to the first state information, among the plural second electronic cassettes 15.

Figure 12:
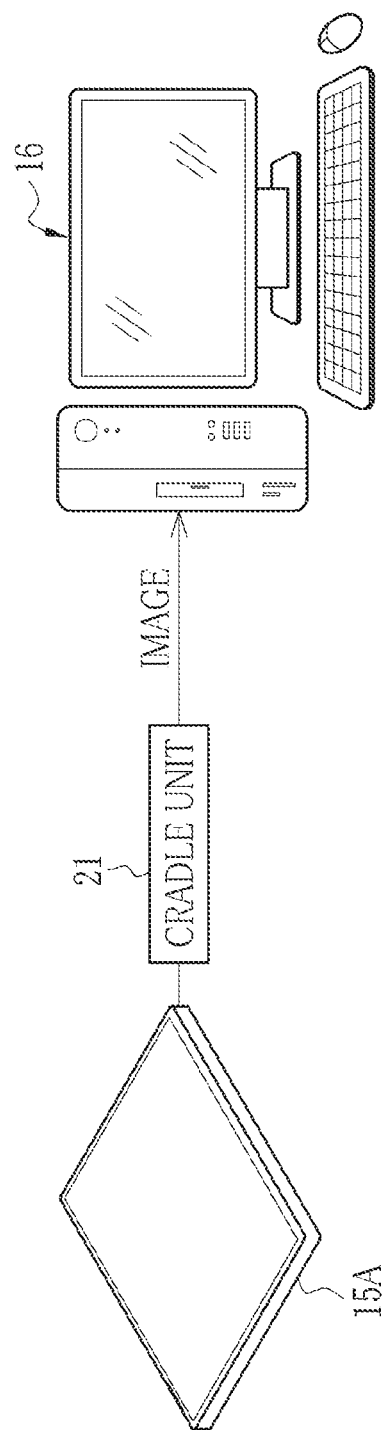
FIG. 12 is a block diagram schematically illustrating a normal transmission mode.
Figure 13:
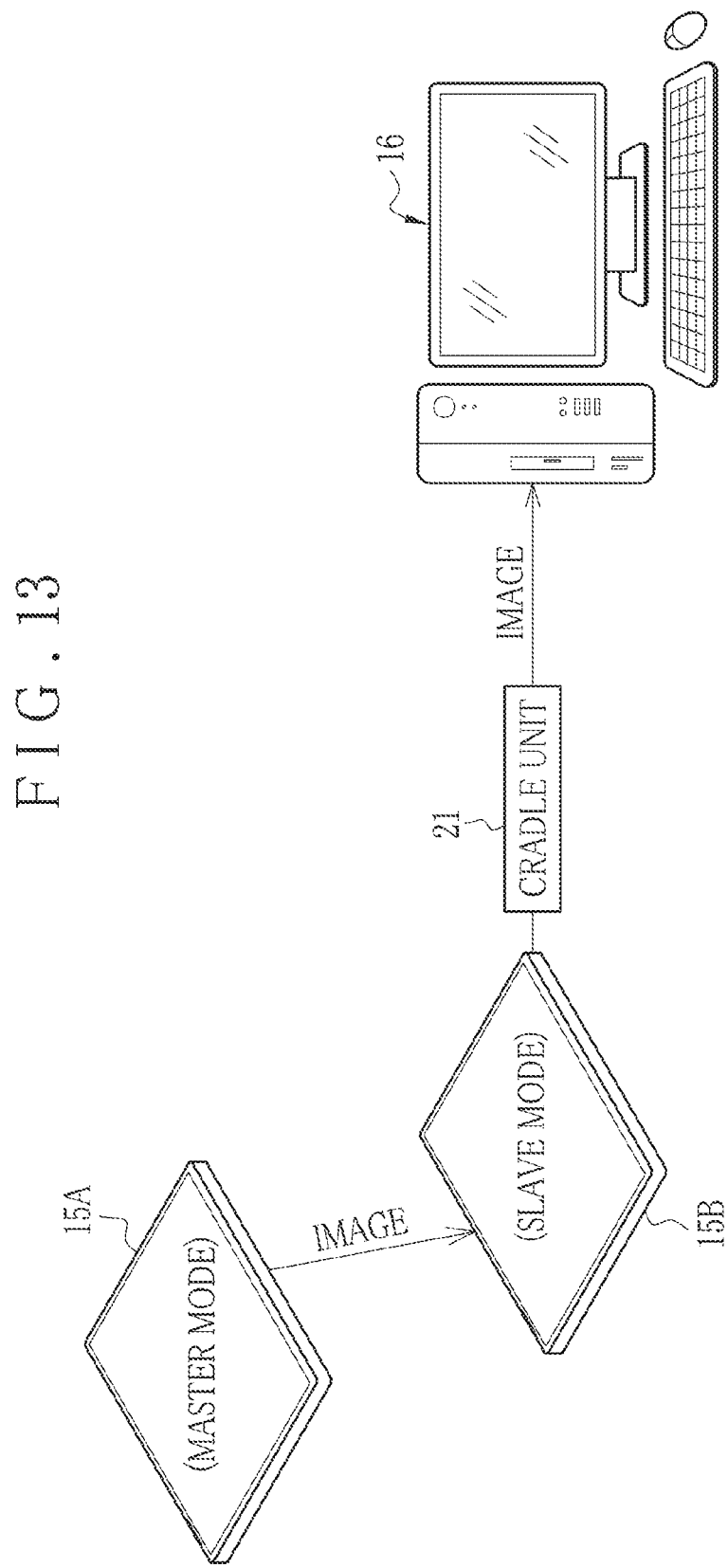
FIG. 13 is a block diagram schematically illustrating a relay transmission mode.

The mode control unit 83 changes over the transmission of the radiation image between a normal transmission mode and a relay transmission mode. In FIG. 12, the normal transmission mode is for transmission of the image from a first electronic cassette 15A as a sender for radiographic imaging to the console device 16 in a direct path without use of the second electronic cassette 15B. In FIG. 13, the relay transmission mode is for wireless transmission of the image from the first electronic cassette 15A to the second electronic cassette 15B specified by the cassette selection unit 82 in the first electronic cassette 15A, and then transmission of the image from the second electronic cassette 15B of relay to the console device 16.

In the case of a state other than the specific state, the mode control unit 83 sets the transmission in the normal transmission mode. In the case of the specific state, the mode control unit 83 sets the transmission in the relay transmission mode. In the embodiment, the electronic cassette 15 in any of the normal and relay transmission modes transmits the radiation image to the console device 16 via the cradle unit 21, the electronic cassette 15 being the first electronic cassette 15A in the normal transmission mode, the electronic cassette 15 being the second electronic cassette 15B in the relay transmission mode.

Assuming that the memory 67 in the first electronic cassette 15A becomes short of an available memory space suitable for storing at least one frame of a radiation image, then the specific state detector 80, the first data acquisition unit 81, the cassette selection unit 82 and the mode control unit 83 make it possible to change over the transmission of the radiation image to the relay transmission mode, wirelessly to transmit the radiation image to the second electronic cassette 15B determined as the functional cassette according to the first state information. Thus, an available memory space for storing at least one frame of the radiation image can be maintained in the memory 67 of the first electronic cassette 15A, to continue the mobile imaging by use of the first electronic cassette 15A.

In FIG. 11, the specific state detector 80 acquires information of an available memory space from the memory 67 after the image readout. The specific state detector 80 compares the acquired available memory space with a predetermined space threshold. An internal memory 84 in the controller 70 stores the space threshold. An example of the space threshold is a lowest value for storing one frame of a radiation image.

Assuming that the available memory space obtained from the memory 67 is equal to or more than the space threshold, then the specific state detector 80 judges that the electronic cassette 15 is not in the specific state (but in the non-specific state or normal functionality), and outputs a flag signal of the non-specific state to the mode control unit 83. Assuming that the available memory space obtained from the memory 67 is less than the space threshold, then the specific state detector 80 judges that the electronic cassette 15 is in the specific state, and outputs a flag signal of the specific state to the mode control unit 83.

The radio communication unit 42 in a normal state operates in the slave mode. Assuming that the available memory space of the memory 67 is less than the space threshold and assuming that the flag signal of the specific state is received from the specific state detector 80, the mode control unit 83 changes over the radio communication unit 42 from the slave mode to the master mode. Then the radio communication unit 42 is operated as an access point.

In the master mode, the radio communication unit 42 operates in the connecting sequence of FIG. 10, and establishes a communication link with an additional electronic cassette 15 operating in the slave mode in an area of the reach of the beacon. In the embodiment, the electronic cassette 15 of which the radio communication unit 42 is the access point is the first electronic cassette 15A. The additional electronic cassette in the slave mode is the second electronic cassette 15B.

The mode control unit 83 upon receiving the flag signal of the specific state from the specific state detector 80 causes the first data acquisition unit 81 to acquire the first state information. The first data acquisition unit 81 outputs a request for the information acquisition to the radio communication unit 42. The request is for requesting a wireless transmission of the first state information to the second electronic cassette 15B. The radio communication unit 42 wirelessly transmits the request from the first data acquisition unit 81 to the second electronic cassette 15B with which the communication link is established.

Figure 14:
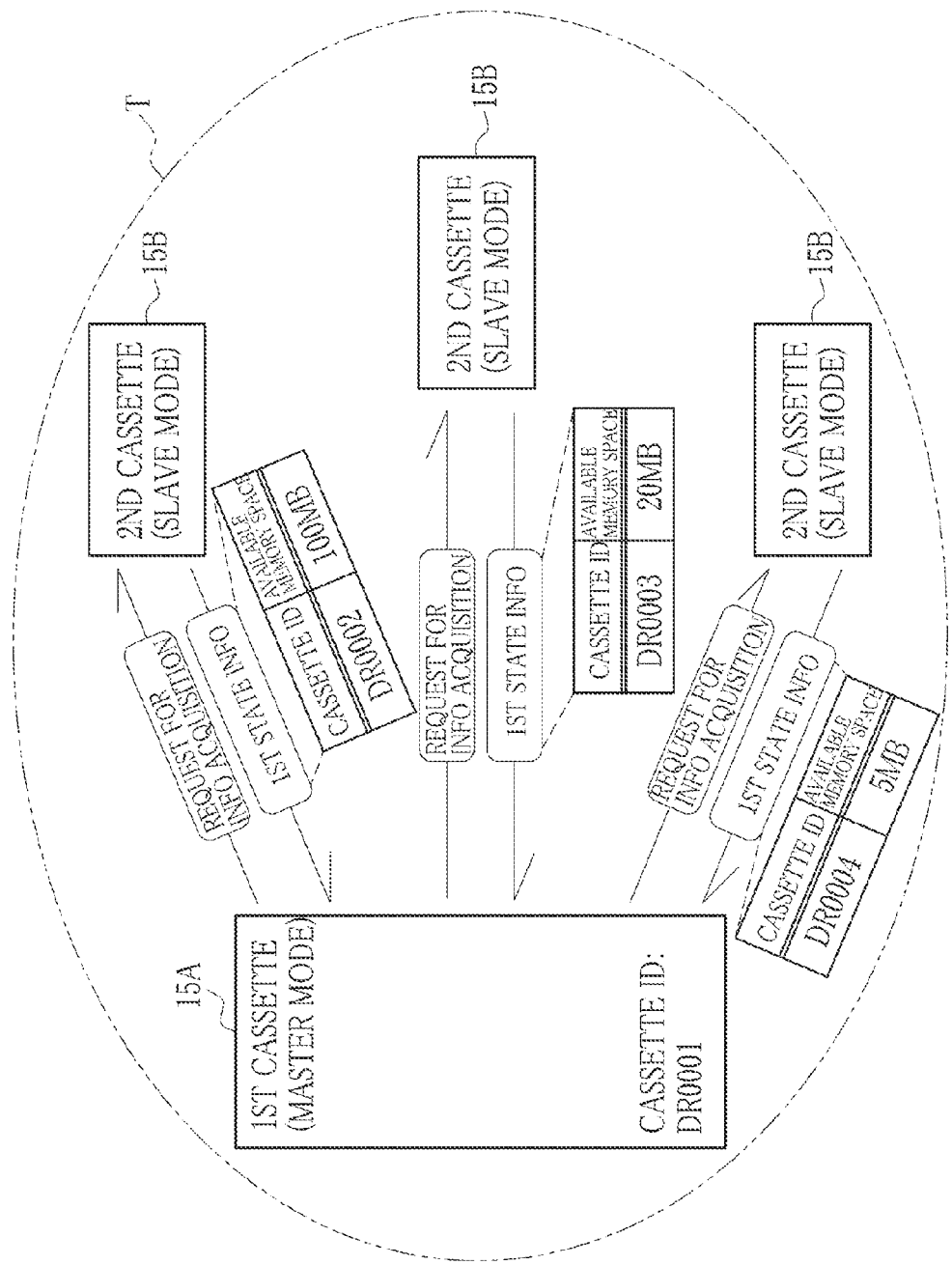
FIG. 14 is a block diagram schematically illustrating radio communication to transmit a request and first state information.

In FIG. 14, the second electronic cassette 15B upon wireless reception of the request for information acquisition from the first electronic cassette 15A transmits the first state information to the first electronic cassette 15A wirelessly. Data in the first state information includes a cassette ID of the second electronic cassette 15B and available memory space of the memory 67 in the second electronic cassette 15B.

In FIG. 14, the three second electronic cassettes 15B with cassette IDs of DR0002, DR0003 and DR0004 are present in an area T of the phantom line of the reach of the beacon from the radio communication unit 42 of the first electronic cassette 15A with a cassette ID of DR0001. The first electronic cassette 15A wirelessly transmits a request for information acquisition to the three second electronic cassettes 15B, each of which wirelessly transmits the first state information to the first electronic cassette 15A. In the embodiment, the second electronic cassette 15B is the electronic cassette 15 placed in the medical cart 11 together with the first electronic cassette 15A.

In FIG. 11, the first data acquisition unit 81 receives the first state information from the radio communication unit 42, and outputs the first state information to the cassette selection unit 82. The cassette selection unit 82 determines a functional cassette according to the first state information from the first data acquisition unit 81 and information of the space threshold from the internal memory 84. The cassette selection unit 82 determines the second electronic cassette 15B as the functional cassette on a condition of an available memory space of first state information being the largest and being equal to or more than the space threshold. The cassette selection unit 82 outputs a cassette ID of the second electronic cassette 15B as the functional cassette to the mode control unit 83.

Let the space threshold be as large as 2 MB (megabytes). In FIG. 14, the second electronic cassette 15B with the cassette ID of DR0002 has the available memory space of 100 MB. The second electronic cassette 15B with the cassette ID of DR0003 has the available memory space of 20 MB. The second electronic cassette 15B with the cassette ID of DR0004 has the available memory space of 5 MB. Accordingly, the second electronic cassette 15B with the cassette ID of DR0002 is determined as a functional cassette because the available memory space is the largest and equal to or more than the space threshold. The cassette ID of DR0002 is output to the mode control unit 83.

Figure 15:
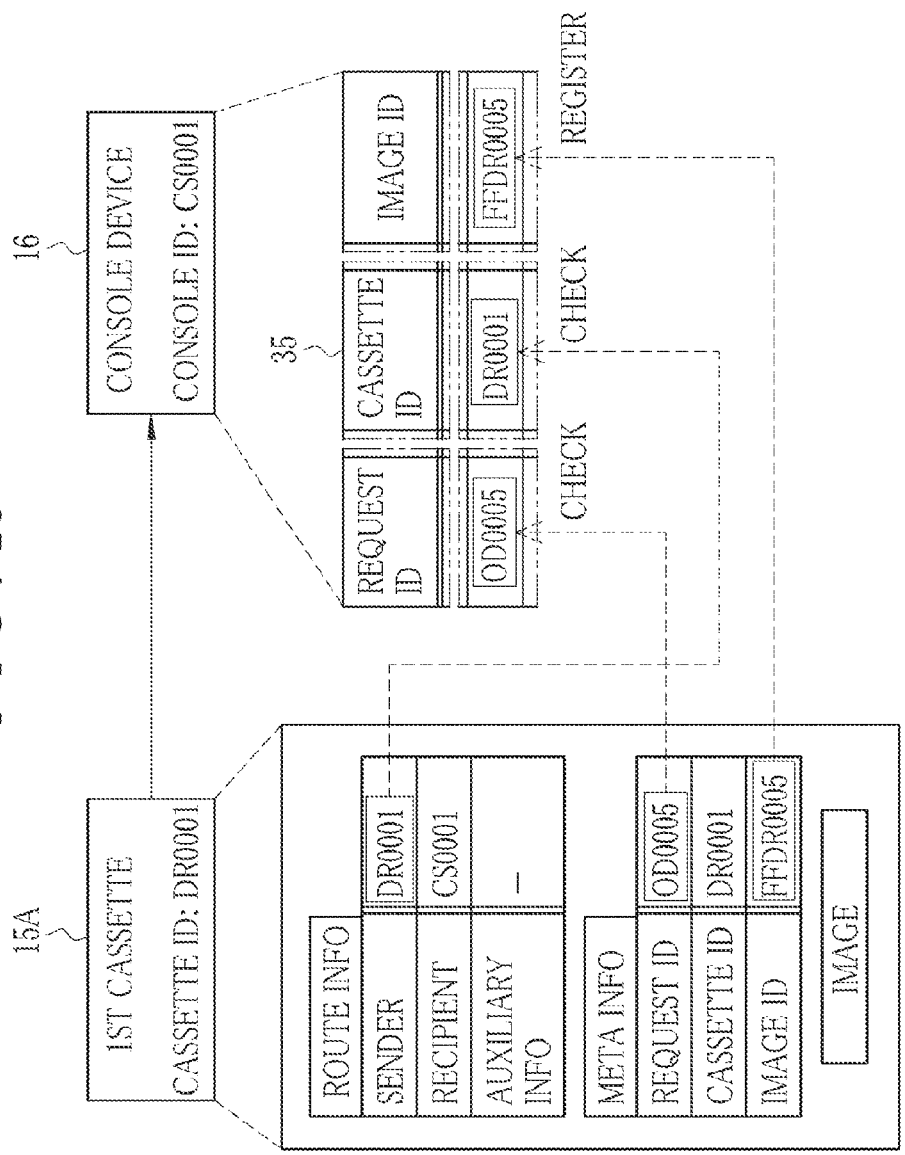
FIG. 15 is a data chart illustrating information of communication in a normal transmission mode.
Figure 16:
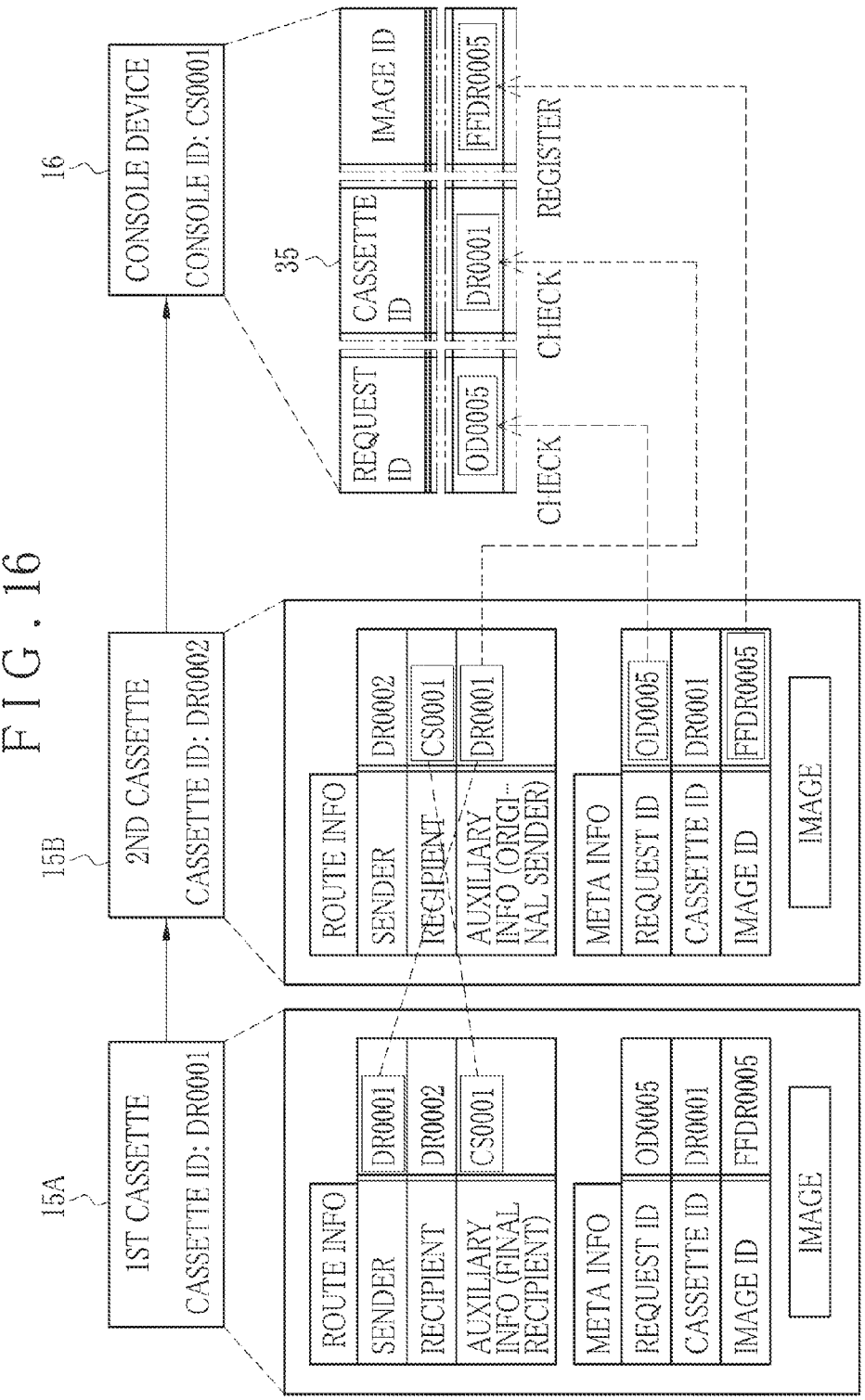
FIG. 16 is a data chart illustrating information of communication in the relay transmission mode.

In FIGS. 15 and 16, the radiation image is transmitted together with the route information (addressing information) and meta information. The route information is for notifying the radio communication unit 42 or the wired communication interface 43 of the recipient of the radiation image, and is produced by the mode control unit 83. Data in the route information are a sender and recipient of the radiation image, and auxiliary data. Data in the meta information include a request ID, cassette ID and image ID.

FIG. 15 illustrates the normal transmission mode. The mode control unit 83 in the first electronic cassette 15A sets the cassette ID of the first electronic cassette 15A for a data item of the sender in the route information (addressing information), and sets the console ID of the console device 16 for a data item of the recipient. The console ID is read from the internal memory 84 to the mode control unit 83. Note that no ID is set for a data item of the auxiliary information in the normal transmission mode.

The console device 16 receives the radiation image from the first electronic cassette 15A together with the route information (addressing information) and meta information. The console device 16 checks the request ID in the meta information and the request ID registered in the request list 35, and then checks the cassette ID set in a data item of the sender in the route information and the cassette ID registered in the request list 35. Thus, the console device 16 can recognize a request ID of one of the radiation images in the request list 35 corresponding to the received radiation image, and identification of the sender of the radiation image with the cassette ID registered in the request list 35.

Assuming that the request ID set in the meta information is registered in the request list 35 and assuming that the cassette ID set in the data item of the sender in the route information (addressing information) is identical with the cassette ID registered in the request list 35, then the console device 16 registers an image ID of the meta information for a data item of the image ID in the request list 35.

In FIG. 16, the relay transmission mode is illustrated. The mode control unit 83 in the first electronic cassette 15A sets the cassette ID of the first electronic cassette 15A for a data item of the sender in the route information (addressing information) in the same manner as the normal transmission mode.

However, the mode control unit 83 does not set the console ID of the console device 16 in the normal transmission mode for a data item of the sender in the route information (addressing information), but sets the cassette ID of the functional cassette from the cassette selection unit 82. Also, the mode control unit 83 sets the console ID from the internal memory 84 for a data item of the auxiliary information by way of a final recipient of the radiation image.

The second electronic cassette 15B receives the radiation image from the first electronic cassette 15A with the route information (addressing information) and meta information. The mode control unit 83 in the second electronic cassette 15B sets the cassette ID of itself for a data item of the sender in the route information. The mode control unit 83 in the second electronic cassette 15B writes the console ID of the auxiliary information of the route information from the first electronic cassette 15A to a data item of the sender, and writes the cassette ID of the first electronic cassette 15A set for the sender in the route information from the first electronic cassette 15A to a data item of the auxiliary information. Note that the auxiliary information is an expression of original sender information that the first electronic cassette 15A is an original sender of the radiation image.

The console device 16 receives the radiation image from the second electronic cassette 15B together with the route information (addressing information) and meta information. The console device 16 checks the request ID set in the meta information and the request ID registered in the request list 35 in the same manner as the normal transmission mode. The console device 16 checks the cassette ID registered in the request list 35 in the same manner as the normal transmission mode. The cassette ID of the first electronic cassette 15A as an original sender is registered in the data item of the auxiliary information of the route information (addressing information). The console device 16 checks the cassette ID in the data item of the auxiliary information of the route information and the cassette ID registered in the request list 35, without checking the cassette ID in the data item of the sender in the route information. Succeeding steps after this are the same as those for the normal transmission mode. Thus, the mode control unit 83 changes over the normal and relay transmission modes by changing information for the route information.

After the radiation image is transmitted to the second electronic cassette 15B in the relay transmission mode, the mode control unit 83 changes over the transmission to the normal transmission mode again. The radio communication unit 42 is caused to operate in the slave mode.

Figure 17:
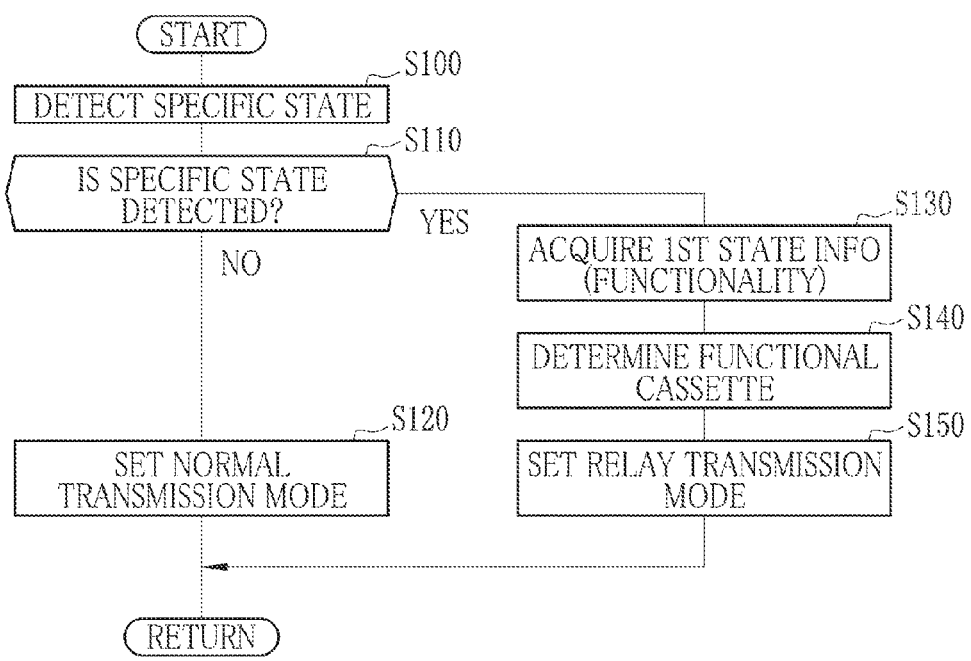
FIG. 17 is a flow chart illustrating operation of the controller.

The operation of the construction is described now by referring to FIG. 17. In the mobile imaging of FIG. 2, the operator OP selects the electronic cassette 15 and sets an imaging condition for imaging in response to a request or requirement for the mobile imaging. The information in the request list 35 is printed on paper material, which he or she carries manually. Then the electronic cassette 15 for imaging is taken out of the cradle unit 21 in the examination room 18, moved into the storage room 17, and placed in the medical cart 11. He or she moves from the storage room 17 to the patient room 20 together with the medical cart 11.

The operator OP upon reaching the patient room 20 checks the information in the request list 35 visually by use of the paper material, and confirms correspondence of the patient P to the electronic cassette 15, the imaging condition (menu for the object) and the like. He or she manually inputs the exposure condition in the source control unit 14, the exposure condition being equal to that corresponding to the imaging condition, or being after fine adjustment in compliance with a body size or the like of the patient P on the basis of the set imaging condition.

The operator OP positions the radiation source 13, the electronic cassette 15 and the patient P suitably. For example, the electronic cassette 15 is placed between the patient P and the bed 19. Then the radiation source 13 is driven to emit X-rays to the patient P. The X-rays transmitted through the patient P are detected by the electronic cassette 15, which generates a radiation image or X-ray image.

In FIG. 17, the specific state detector 80 acquires information of the available memory space of the memory 67 after the image readout in a step S100. The specific state detector 80 compares the acquired available memory space with the space threshold, so as to check occurrence of the specific state in which the available memory space is short of a size sufficient for storing at least one frame of the radiation image.

Assuming that the available memory space acquired from the memory 67 is equal or more than the space threshold, the specific state detector 80 judges a non-specific state (normal functionality) which is different from the specific state (no in a step S110). The specific state detector 80 outputs a flag signal of the non-specific state to the mode control unit 83. Then the specific state detector 80 sets the normal transmission mode in a step S120. In the normal transmission mode, the mode control unit 83 sets the console ID read from the internal memory 84 to a data item of the recipient of the radiation image in the route information (addressing information).

Assuming that the available memory space of the memory 67 is less than the space threshold, the specific state detector 80 judges the specific state (yes in the step S110). The specific state detector 80 outputs a flag signal of the specific state to the mode control unit 83.

In case the specific state detector 80 outputs the flag signal of the specific state, the mode control unit 83 changes over the radio communication unit 42 from the slave mode to the master mode. The radio communication unit 42 comes to operate as an access point.

A communication link is established between the first electronic cassette 15A having the radio communication unit 42 as the access point, and the second electronic cassette 15B. A request for information acquisition and the first state information are transmitted between those wirelessly. Thus, the first data acquisition unit 81 (for monitoring functionality) acquires the first state information a step S130. The first state information is output to the cassette selection unit 82.

The cassette selection unit 82 determines the second electronic cassette 15B for a functional cassette (relay cassette) on a condition of having the largest available memory space which is equal to or more than the space threshold, in a step S140. A cassette ID of the functional cassette is output to the mode control unit 83.

The mode control unit 83 changes over the transmission to the relay transmission mode in case the specific state detector 80 outputs the flag signal of the specific state, in a step S150. In the relay transmission mode, the mode control unit 83 sets the cassette ID of the functional cassette from the cassette selection unit 82 to a data item of the recipient of the radiation image in the route information (addressing information). The console ID from the internal memory 84 is set to a data item of the auxiliary information. The radiation image is transmitted to the second electronic cassette 15B determined as the functional cassette.

The operator OP moves between the patient rooms 20 to one another for mobile imaging, and then returns to the examination room 18 together with the medical cart 11. The operator OP removes the electronic cassette 15 from the medical cart 11, and sets the electronic cassette 15 in the cradle unit 21. The electronic cassette 15 transmits the radiation image to the console device 16 (user terminal device) by use of the cradle unit 21.

In the normal transmission mode, the first electronic cassette 15A transmits the radiation image to the console device 16 with the route information (addressing information) and meta information. In the relay transmission mode, the second electronic cassette 15B transmits the radiation image to the console device 16 with the route information and meta information.

In the normal transmission mode, the console device 16 checks the request ID set in the meta information and the request ID registered in the request list 35, and then checks the cassette ID set with a data item of the sender in the route information (addressing information) and the cassette ID registered in the request list 35. In the relay transmission mode, the console device 16 checks the request ID set in the meta information and the request ID registered in the request list 35, and then checks the cassette ID set with a data item of auxiliary information of the route information and the cassette ID registered in the request list 35. Thus, the console device 16 recognizes a request ID of one of the radiation images in the request list 35 corresponding to the received radiation image, and identification of the sender of the radiation image with the cassette ID registered in the request list 35.

The console device 16 displays the radiation image received from the electronic cassette 15, for the operator OP to view the radiation image.

For the mobile imaging, the electronic cassette 15 is taken out of the cradle unit 21 and moved away from the examination room 18. The electronic cassette 15 is off-line from the console device 16. Assuming that the transmission mode is only the normal transmission mode, an available memory space of the memory 67 of the first electronic cassette 15A becomes too small in the course of the mobile imaging. Assuming that additional imaging should be performed with the first electronic cassette 15A, the following complicated steps are required.

To be precise, it is necessary to return the medical cart 11 to the examination room 18 by interrupting the mobile imaging, store the first electronic cassette 15A in the cradle unit 21, connect the first electronic cassette 15A with the console device 16 via the cradle unit 21, and transmit the radiation image to the console device 16 to restart the mobile imaging by reliably using an available memory space in the memory 67 of the first electronic cassette 15A.

Assuming that the memory 67 in the first electronic cassette 15A becomes short of the available memory space, it may be possible to conceive a use of the second electronic cassette 15B with a sufficient available memory space in the memory 67 in place of the first electronic cassette 15A for imaging. However, the electronic cassette 15 for use is associated with the request for imaging in combination with the request ID and cassette ID in the request list 35. It is impossible to associate the request with the radiation image in the console device 16. Assuming that the type of the second electronic cassette 15B is different from that of the first electronic cassette 15A, the second electronic cassette 15B cannot be used instead of the first electronic cassette 15A for imaging. The above-described complicated operation may be required.

In contrast, the relay transmission mode is utilized in the embodiment. Assuming that the memory 67 in the first electronic cassette 15A is short of the available memory space, the transmission is changed over to the relay transmission mode, wirelessly to transmit the radiation image to the second electronic cassette 15B. The memory 67 of the second electronic cassette 15B stores the radiation image in a temporary manner. Thus, it is unnecessary to return to the examination room 18 with the medical cart 11 by interrupting the mobile imaging, and to return the first electronic cassette 15A to the cradle unit 21. It follows that the operator OP can perform the mobile imaging smoothly.

In the relay transmission mode, the console device 16 receives the radiation image from the second electronic cassette 15B different from the first electronic cassette 15A of which the cassette ID is registered in the request list 35. A request for imaging cannot be checked for correspondence to the radiation image. However, the cassette ID of the first electronic cassette 15A is transferred and stored in the data item in the auxiliary information by use of the second electronic cassette 15B, to constitute information of the radiation image for an origin (sender) of the first electronic cassette 15A. Thus, the console device 16 can check the request for imaging for correspondence to the radiation image.

The radio communication unit 42 of the first electronic cassette 15A operates as the access point for radio communication with the second electronic cassette 15B. The first electronic cassette 15A acquires the first state information of the status of the second electronic cassette 15B, so that a functional cassette is determined according to the first state information. Actually, the console device 16 is irrespective of determination of the functional cassette. It is possible to store the radiation image from the first electronic cassette 15A in the memory 67 of the second electronic cassette 15B in a temporary manner even in the absence of the console device 16, for example, inside the patient room 20 as a location of the mobile imaging.

Also, the use of the relay transmission mode for the radiation image can establish a workflow of the mobile imaging in the same manner as the conventional use of a film cassette, IP cassette or CR cassette without a mobile structure of the console device 16.

Note that the cradle unit 21 may not be used. The radio communication unit 42 of the electronic cassette 15 can be operated as an access point. A radio communication unit can be incorporated in the console device 16 to operate in the slave mode. A communication link can be established between the electronic cassette 15 and the console device 16, wirelessly to transmit the imaging condition (menu for the object) or radiation image.

Second Embodiment

In the first embodiment, the radiation image is transmitted from the cradle unit 21 to the console device 16 (user terminal device) after the return from the patient room 20 of the mobile imaging to the examination room 18. However, it is possible in radiographic imaging in the examination room 18 to use the radio communication unit 42 as an access point in the electronic cassette 15 for use in the imaging. Wireless communication between the electronic cassette 15 and the console device 16 can be established to transmit the radiation image from the electronic cassette 15 to the console device 16.

In the mobile imaging, the radiation image cannot be checked in the console device 16 until the electronic cassette 15 is set again in the cradle unit 21 in the examination room 18 after completing the mobile imaging in relation to all of the patient rooms 20 in a planned workflow. However, it is possible in the imaging in the examination room 18 to transmit a radiation image to the console device 16 immediately after the imaging by use of the relay of the radio communication provided by the radio communication unit 42 as an access point. The radiation image can be viewed in the real-time manner.

However, failure in communication is likely to occur due to a distance between the electronic cassette 15 in the examination room 18 and the console device 16 in the storage room 17. In view of this problem, the radio communication unit 42 of the second electronic cassette 15 is operated as an access point in case the normal transmission mode is unavailable while failure occurs due to a distance between the electronic cassette 15 and the console device 16. The radio communication of the radio communication unit 42 of the second electronic cassette 15 for relay is utilized to transmit the radiation image to the console device 16 via the radio communication unit 42 of the second electronic cassette 15.

Figure 18:
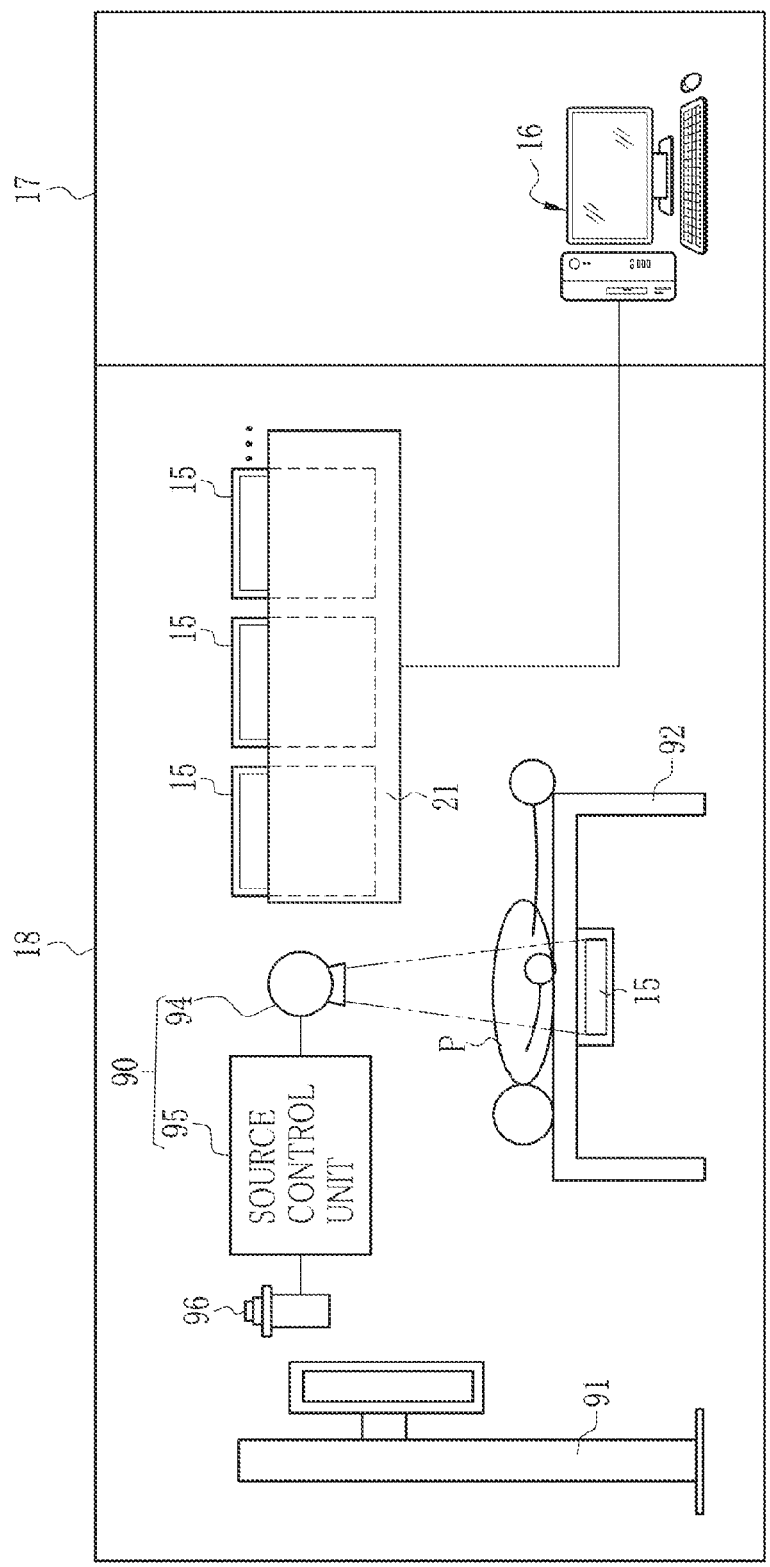
FIG. 18 is a block diagram schematically illustrating radiographic imaging in a second preferred embodiment.

In FIG. 18, the examination room 18 contains the cradle unit 21 and also a radiation generator 90 or X-ray generator, a floor stand 91 for radiographic imaging, and a patient table 92 for radiographic imaging. The radiation generator 90 is an installed type for use. The floor stand 91 is used for imaging a patient body P in a standing posture (upright posture). The patient table 92 is used for imaging the patient body P in a lying posture. In the drawing, the electronic cassette 15 is set in the patient table 92 for radiographic imaging of the patient body P in the lying posture.

The radiation generator 90 includes a radiation source 94 or X-ray source and a source control unit 95 for controlling the radiation source 94. There is a radiation switch 96 in the source control unit 95. The radiation source 94 is used commonly by the floor stand 91 and the patient table 92. Note that structures of the radiation source 94, the source control unit 95 and the radiation switch 96 are the same as the radiation source 13, the source control unit 14 and the radiation switch 22 of the first embodiment.

In the embodiment, the radio communication unit 42 of the electronic cassette 15 for imaging is in the master mode and operates as the access point. The radio communication unit 42 of the other electronic cassette 15 operates in the slave mode in the same manner as the first embodiment.

The specific state of the embodiment is a state of impossibility of using the normal transmission mode. Examples of the specific state include a state of presence of an intermediate object between the electronic cassette 15 and the console device 16 for blocking radio waves, or other statuses without receiving a beacon from the radio communication unit 42 of the electronic cassette 15 at the console device 16.

Figure 19:
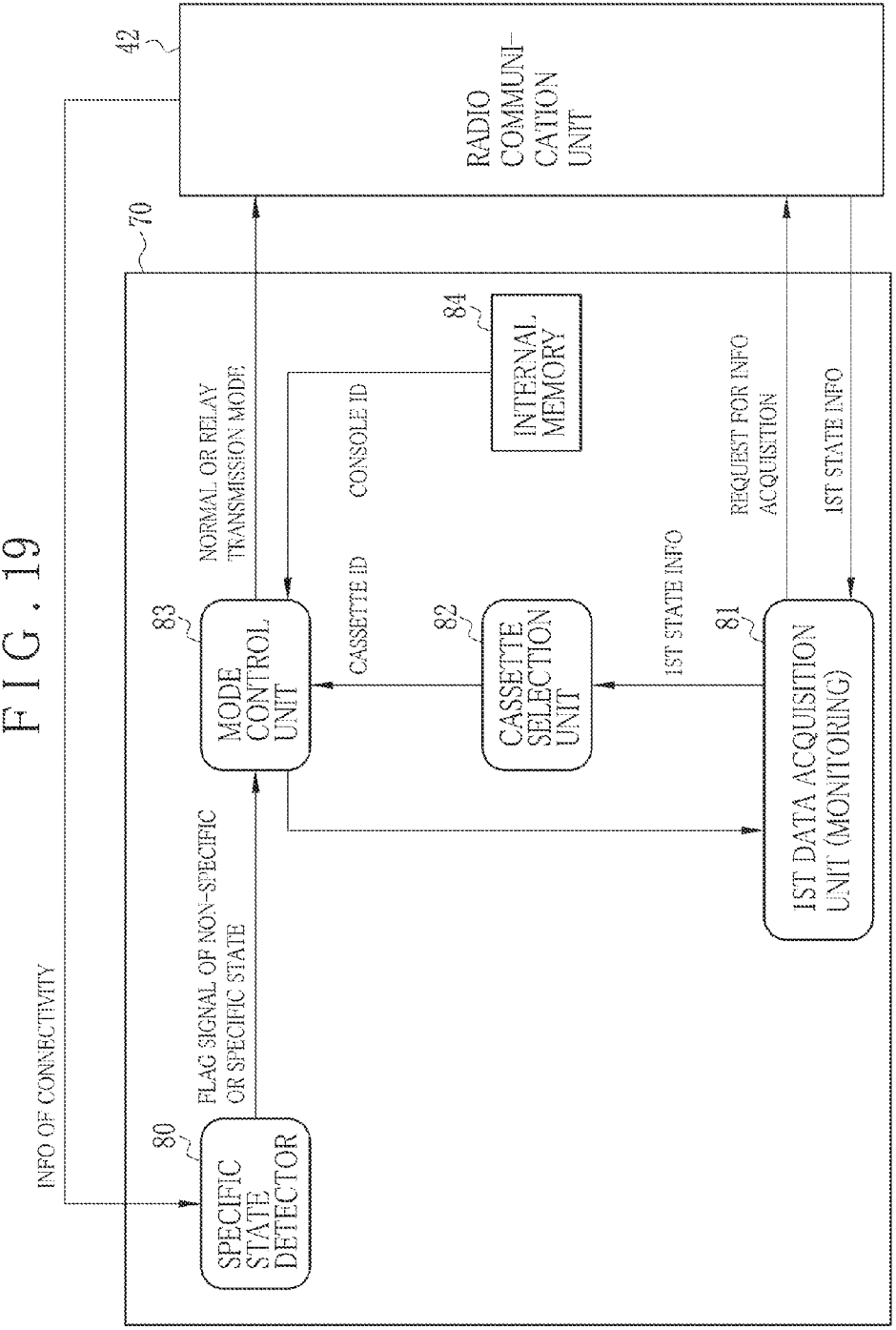
FIG. 19 is a block diagram schematically illustrating the controller.

In FIG. 19, the specific state detector 80 of the embodiment acquires information of connectivity (communication state) with the console device 16 from the radio communication unit 42 after the image readout. Assuming that the radio communication between the radio communication unit 42 and the console device 16 is established, the specific state detector 80 determines a non-specific state (normal functionality) for the electronic cassette 15. Assuming that no radio communication between the radio communication unit 42 and the console device 16 is established, the specific state detector 80 determines the specific state (specific functionality) for the electronic cassette 15.

In the specific state upon detection in the specific state detector 80, the radio communication unit 42 performs a connecting sequence of FIG. 10, to establish a communication link with the other electronic cassette 15 which is in the slave mode and located in an area of reach of the beacon. In the embodiment, the electronic cassette 15 of which the radio communication unit 42 is the access point is the first electronic cassette 15A. The other electronic cassette in the slave mode is the second electronic cassette 15B, in the same manner as the first embodiment. See FIG. 20.

Assuming that the specific state is determined in the specific state detector 80, the first data acquisition unit 81 performs acquisition of the first state information in the same manner as the first embodiment. Although the first state information is transmitted wirelessly inclusive of the information of the available memory space of the memory 67 in the second electronic cassette 15B, the first state information inclusive of the information of the connectivity with the console device 16 is transmitted wirelessly in the embodiment in place of the available memory space of the memory 67. See FIG. 20.

Figure 20:
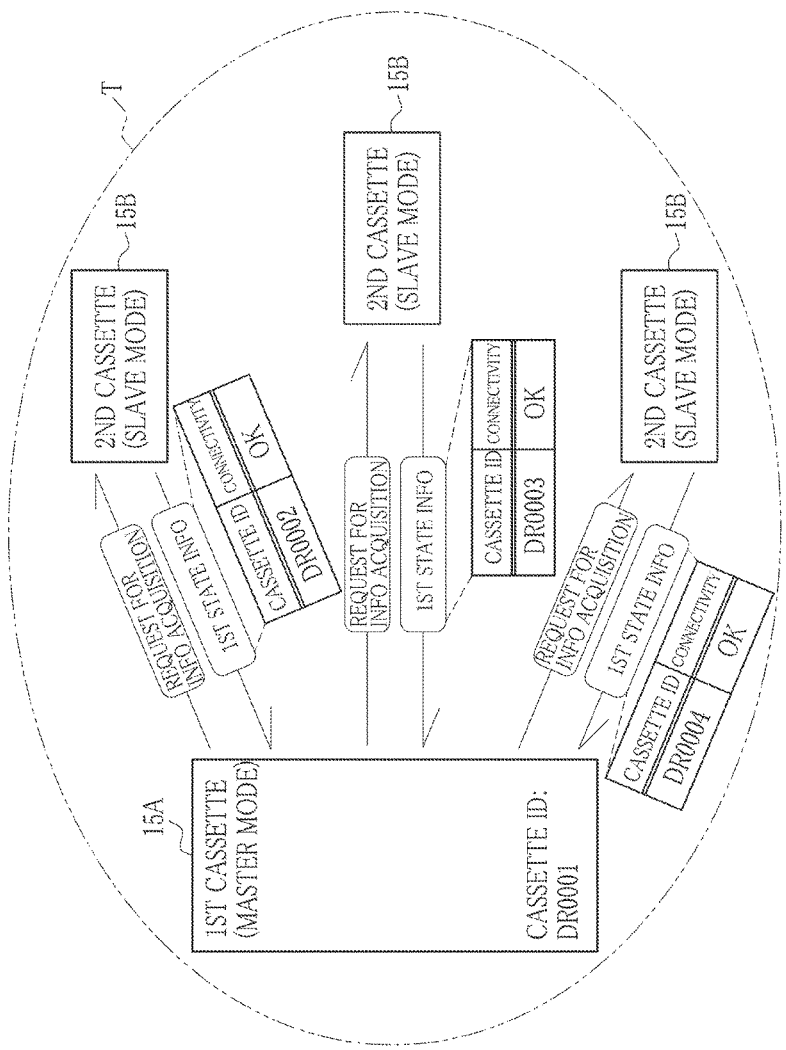
FIG. 20 is a data chart illustrating radio communication to transmit the request and the first state information.

In FIG. 20, wireless transmission of the first state information is illustrated in paths from the three second electronic cassettes 15B to the first electronic cassette 15A, the three second electronic cassettes 15B having the cassette IDs of DR0002, DR0003 and DR0004, and being located in an area T of the phantom lines of the reach of the beacon from the radio communication unit 42 of the first electronic cassette 15A having the cassette ID of DR0001. All the second electronic cassettes 15B are stored in the cradle unit 21. Communication of the second electronic cassettes 15B with the console device 16 is established by means of the cradle unit 21. Connectivity (communication state) is an OK state (normal).

The cassette selection unit 82 determines the second electronic cassette 15B as the functional cassette owing to the established communication with the console device 16 among the plural second electronic cassettes 15B. A cassette ID of the functional cassette is output to the mode control unit 83. All of the three second electronic cassettes 15B in FIG. 20 are on-line with the console device 16 by the established communication. The cassette selection unit 82 determines the second electronic cassette 15B with a cassette ID of DR0002 or the lowest serial number as the functional cassette, and outputs the cassette ID of DR0002.

Figure 21:
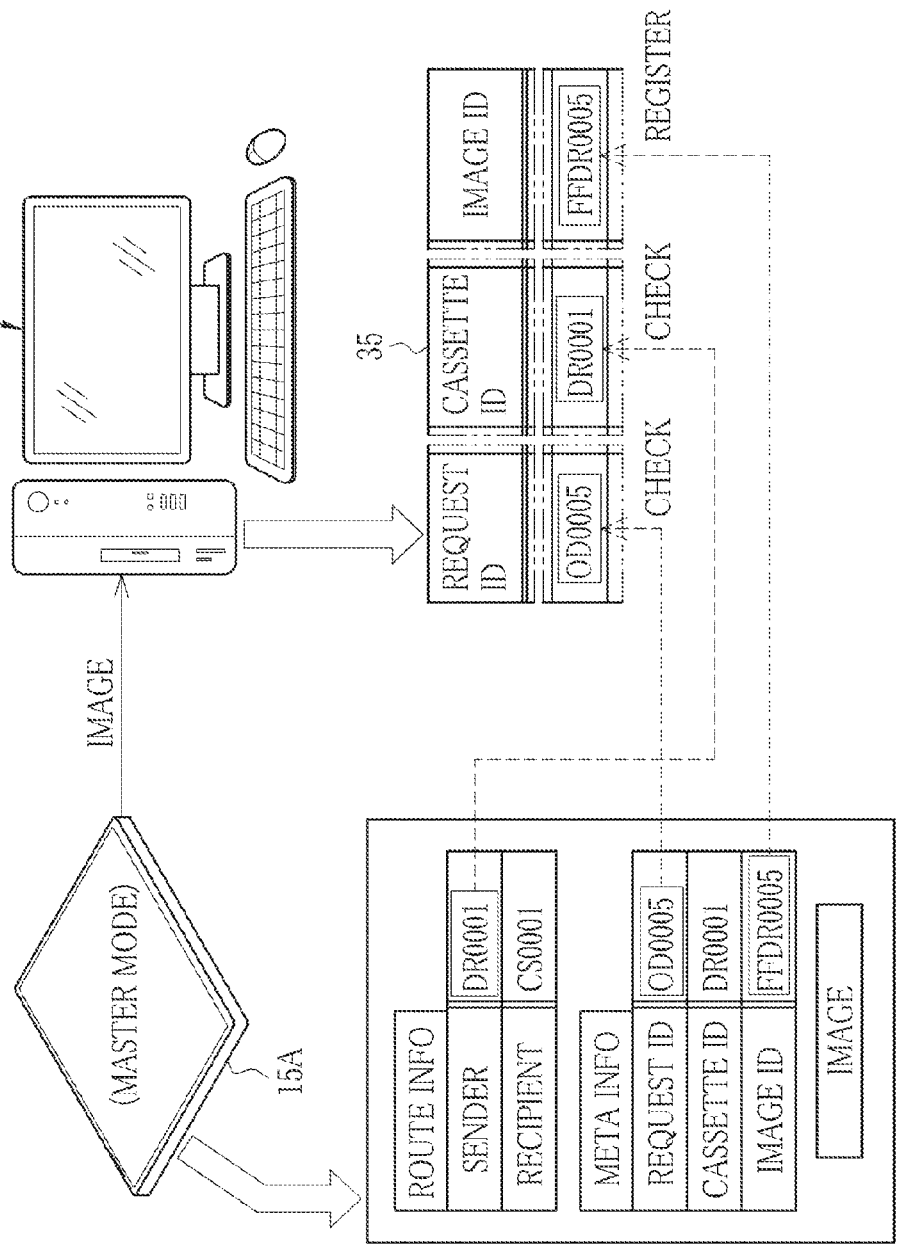
FIG. 21 is a data chart illustrating the normal transmission mode.

The normal transmission mode of the embodiment is for wireless transmission of a radiation image from the first electronic cassette 15A directly to the console device 16 without relay of the second electronic cassette 15B, as illustrated in FIG. 21.

Figure 22:
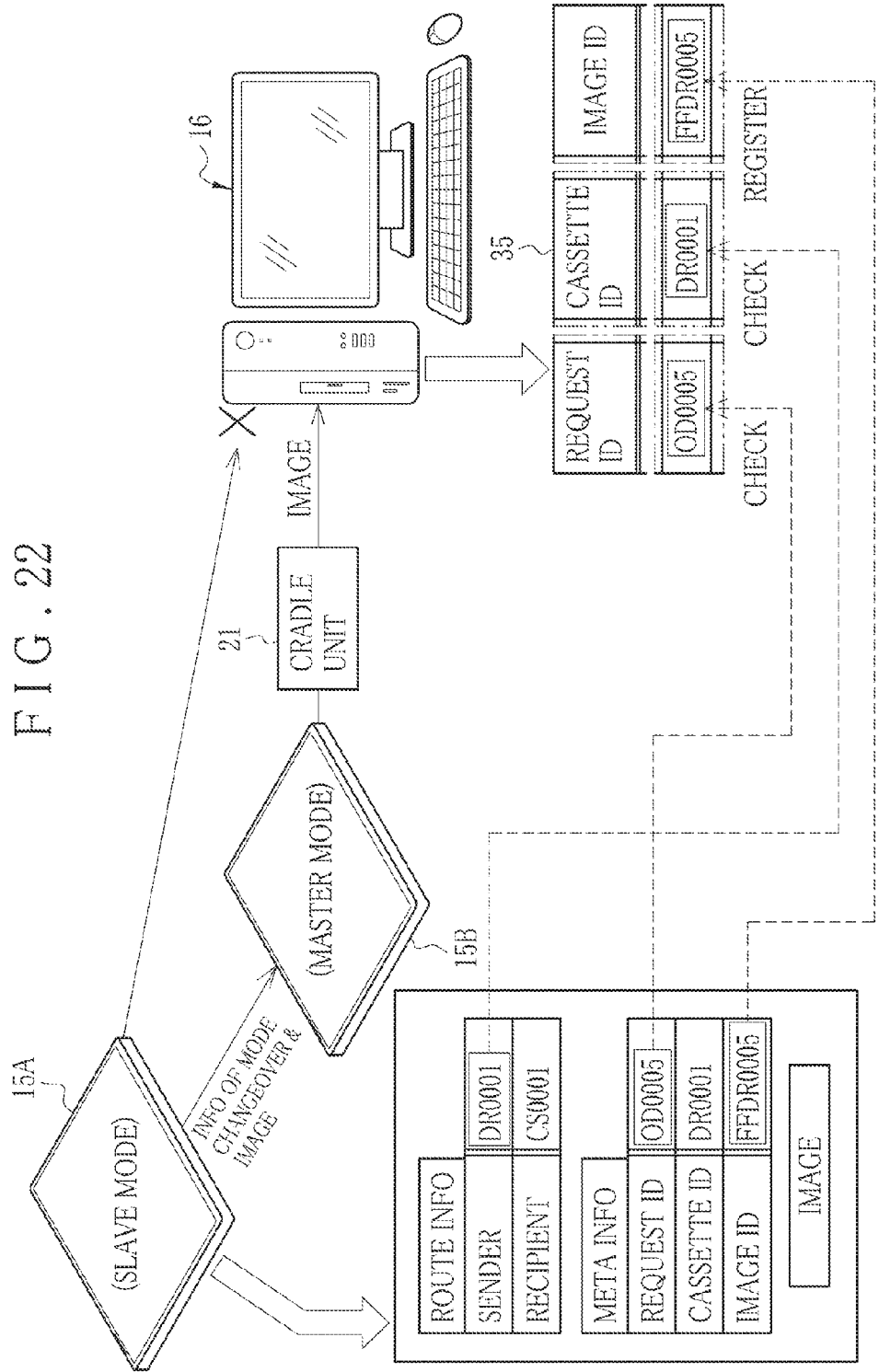
FIG. 22 is a data chart illustrating the relay transmission mode.

In FIG. 22, the relay transmission mode in the embodiment is illustrated. The radio communication unit 42 of the second electronic cassette 15B as the functional cassette operates as the access point. The relay of the radio communication provided by the radio communication unit 42 of the second electronic cassette 15B as the access point is utilized to transmit the radiation image from the first electronic cassette 15A to the console device 16, instead of the use of the radio communication unit 42 of the first electronic cassette 15A. In the relay transmission mode, the radiation image is wirelessly transmitted from the first electronic cassette 15A to the second electronic cassette 15B as the functional cassette. The second electronic cassette 15B transmits the radiation image in a wired manner via the cradle unit 21 to the console device 16.

In the present embodiment, no data item of auxiliary information is associated with the route information (addressing information). See FIGS. 21 and 22. The mode control unit 83 sets the console ID read from the internal memory 84 for a data item of the recipient of the radiation image in the route information in any one of the normal and relay transmission modes.

However, it is necessary in the relay transmission mode to change over the radio communication unit 42 of the second electronic cassette 15B as functional cassette to the master mode to operate as an access point, because the radio communication unit 42 in the second electronic cassette 15B operates in the slave mode. In view of this, the mode control unit 83 of the first electronic cassette 15A causes the radio communication unit 42 wirelessly to transmit information of mode changeover to the second electronic cassette 15B as the functional cassette from the slave mode to the master mode before transmitting the radiation image in the relay transmission mode. See FIG. 22. At the same time, the mode control unit 83 of the first electronic cassette 15A changes over the radio communication unit 42 incorporated therein to the slave mode. The radio communication unit 42 of the second electronic cassette 15B receives the information of the mode changeover, is changed over from the slave mode to the master mode and operates as the access point.

In the second electronic cassette 15B in the relay transmission mode, the radio communication unit 42 operates as the access point, to relay the transmission of the radiation image between the first electronic cassette 15A and the console device 16. No temporary storing of the radiation image in the memory 67 occurs in the second electronic cassette 15B. Thus, it is unnecessary to transmit original sender information from the second electronic cassette 15B to the console device 16 in the manner of the first embodiment.

Should only the normal transmission mode be available for the transmission, a radiation image cannot be transmitted to the console device 16 immediately after the imaging assuming that failure has occurred in the radio communication between the first electronic cassette 15A and the console device 16. The radiation image cannot be checked in the real-time manner. For the purpose of detecting a cause of the communication failure, it is necessary to test operation of the radio communication unit 42 of the first electronic cassette 15A, to check a blocking object of radio waves between the first electronic cassette 15A and the console device 16, and the like as a step unrelated to the radiographic imaging.

Assuming that disconnection occurs in the radio communication between the first electronic cassette 15A and the console device 16, the transmission in the embodiment is changed over to the relay transmission mode. The radio communication unit 42 of the second electronic cassette 15B is operated as an access point instead of the radio communication unit 42 of the first electronic cassette 15A. The radiation image is transmitted from the first electronic cassette 15A to the console device 16 via the second electronic cassette 15B. Thus, viewing the radiation image can be continued in a real-time manner even upon the disconnection in the radio communication between the first electronic cassette 15A and the console device 16. Manipulation unrelated to the imaging is unnecessary. The operator OP can perform the radiographic imaging smoothly in the manner of the first embodiment.

Third Embodiment

A plurality of the electronic cassettes 15 are combined for longitudinal imaging in the field of radiographic imaging, for example, a continuous region including a spine, chest and abdomen, or waist and legs, or other body parts of the patient P. A mode of the longitudinal imaging can be a specific state in the imaging according to the present invention.

Figure 23:
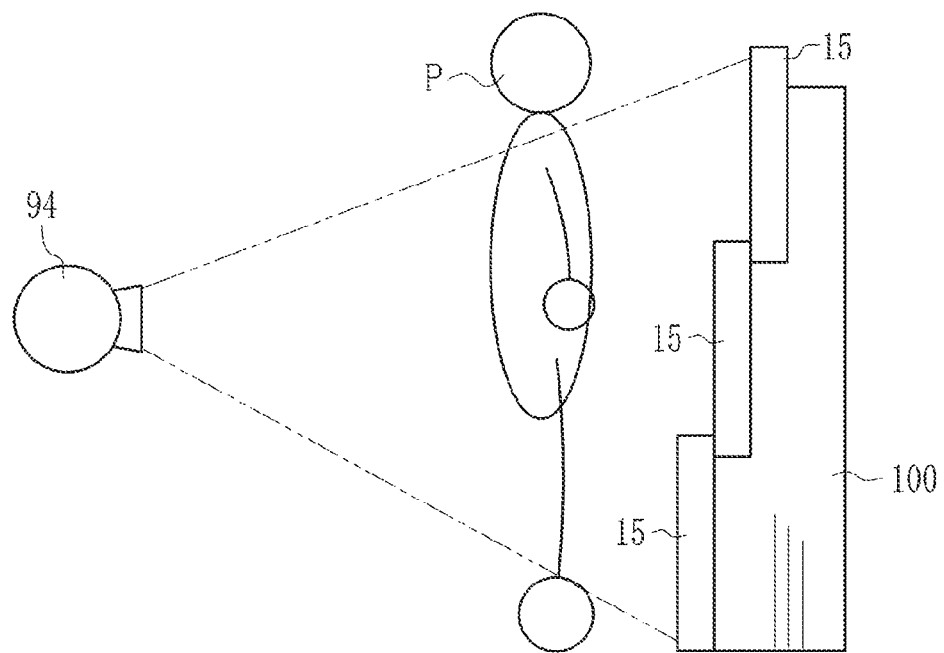
FIG. 23 is an explanatory view in a side elevation illustrating longitudinal imaging in a third preferred embodiment.

In FIG. 23, operation of longitudinal imaging in the examination room 18 of FIG. 18 is illustrated. A special floor stand 100 for radiographic imaging is disposed in the examination room 18 in addition to the floor stand 91 and the patient table 92. The special floor stand 100 has three portions of higher, intermediate and lower heights, and holds at most three of the electronic cassettes 15 arranged vertically in a form with overlapped ends within an exposure field of X-rays. It is possible to use only two of the electronic cassettes 15 for the longitudinal imaging in the special floor stand 100 by positioning those in the higher and intermediate heights or in the intermediate and lower heights.

In the same manner as the first and second embodiments, the operator OP visually checks information in the request for imaging, and determines selection of at least two electronic cassettes 15 and the imaging condition (menu for the object) for imaging. Cassette IDs of the at least two electronic cassettes 15 are registered in association with the request ID of the longitudinal imaging in the request list 35.

Then the operator OP takes out at least two of the electronic cassettes 15 from the cradle unit 21 for use, sets those in the special floor stand 100, and positions the radiation source 94 and the patient P in suitable locations. Then the radiation source 94 is driven to apply X-rays to the patient P. Then the electronic cassettes 15 in the exposure field detect radiation images.

The console device 16 transmits the imaging condition and the exposure condition to one of the electronic cassettes 15 via the cradle unit 21, and simultaneously transmits the information of the mode changeover for the radio communication unit 42 from the slave mode to the master mode. The radio communication unit 42 of the electronic cassette 15 upon receiving the information for the mode changeover is changed over from the slave mode to the master mode, and operates as the access point.

In the connecting sequence of FIG. 10, a communication link is established between the first electronic cassette 15 of which the radio communication unit 42 is the access point and the second electronic cassette 15 operating in the slave mode, in the same manner as the first and second embodiments. Data are wirelessly transmitted, inclusive of an imaging condition (menu for the object) and exposure condition from the electronic cassette 15, and a cassette ID of the electronic cassette 15. In the embodiment, the electronic cassette 15 of which the radio communication unit 42 is the access point is the second electronic cassette 15B. The other electronic cassette in the slave mode is the first electronic cassette 15A. This construction is different from that of the first and second embodiments.

The second electronic cassette 15B is set in the normal transmission mode by the mode control unit 83. The first electronic cassette 15A is changed over to the relay transmission mode by the mode control unit 83. In the first electronic cassette 15A, the mode control unit 83 sets the cassette ID of the second electronic cassette 15B for a data item of a recipient of the radiation image in the route information (addressing information). After the image readout, the first electronic cassette 15A transmits the radiation image to the second electronic cassette 15B. Then the first electronic cassette 15A returns to the normal transmission mode. The second electronic cassette 15B writes the radiation image generated therein and the radiation image from the first electronic cassette 15A to the memory 67, and transmits those images to the console device 16 together.

Figure 24:
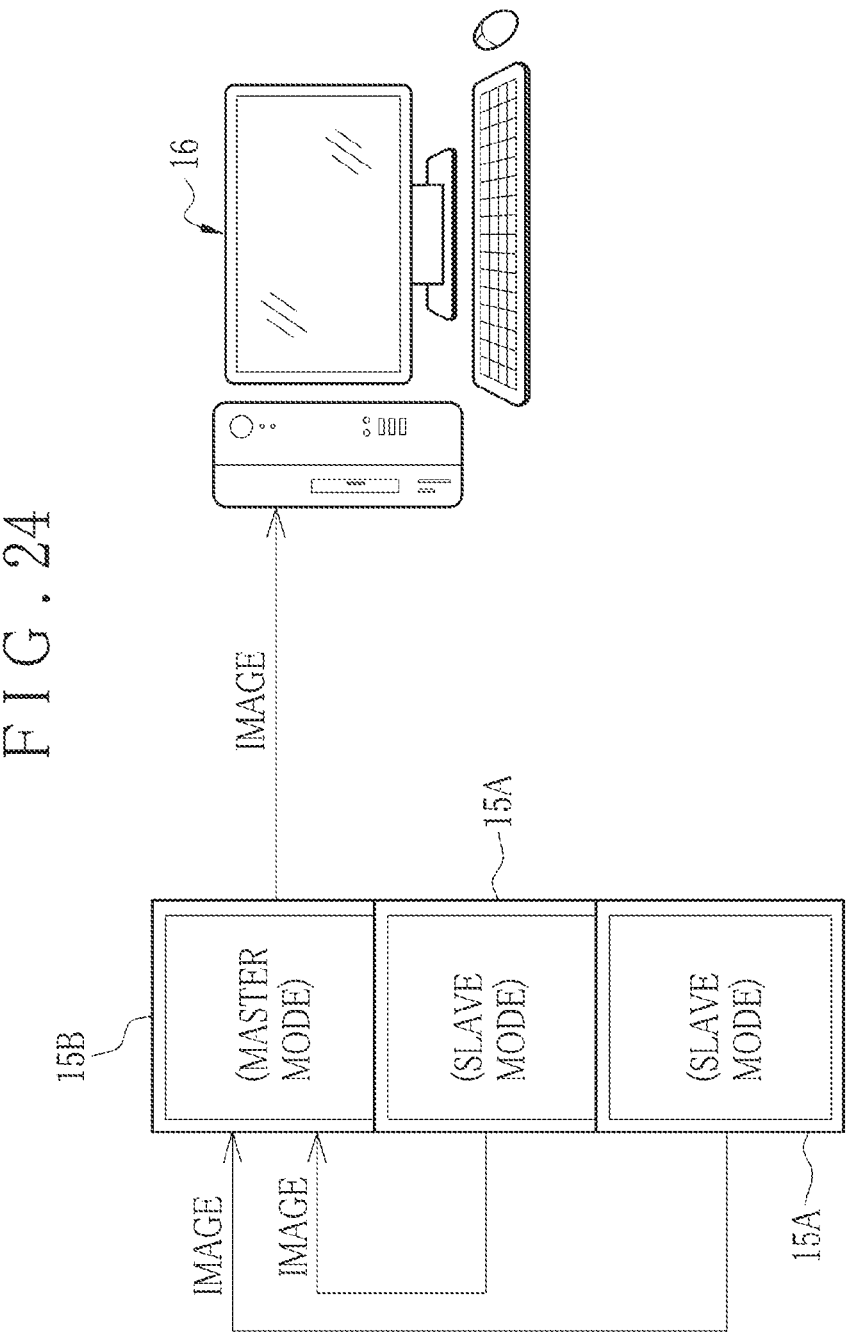
FIG. 24 is a block diagram schematically illustrating transmission of the radiation image.

In FIG. 24, operation of transmitting a radiation image is illustrated on a condition of the second electronic cassette 15B positioned at the higher height in the special floor stand 100, and the first electronic cassettes 15A positioned at the intermediate and lower heights in the special floor stand 100. In FIG. 24, the first electronic cassettes 15A are in the relay transmission mode, and wirelessly transmit radiation images to the second electronic cassette 15B after the image readout. The second electronic cassette 15B writes the radiation image generated therein and the radiation images from the first electronic cassettes 15A to the memory 67.

After the longitudinal imaging, the second electronic cassette 15B wirelessly transmits its radiation image and the radiation images from the first electronic cassette 15A of the intermediate and lower heights to the console device 16. The mode control unit 83 of the second electronic cassette 15B sets the cassette ID of the first electronic cassette 15A for a data item of the auxiliary information in the same manner as the first embodiment.

The console device 16 processes the component radiation images from the second electronic cassette 15B in the image processing of edge correction or the like for smoothing borderlines between the component radiation images. Then the radiation images are combined by image synthesis to produce one continuous composite image. The console device 16 displays the continuous composite image for the operator OP to view. Furthermore, it is possible to perform the edge correction and image synthesis in the controller 70 of the second electronic cassette 15B instead of that by use of the console device 16.

Thus, the first electronic cassette 15 for the longitudinal imaging is set in the normal transmission mode and the remaining electronic cassettes are changed over to the relay transmission mode. The radiation images are collectively received by the first electronic cassette 15 for transmission to the console device 16. Thus, the time of the use of the remaining electronic cassettes can be shortened, to use the remaining electronic cassettes immediately for subsequent imaging after the longitudinal imaging.

In FIG. 24, the second electronic cassette 15B wirelessly transmits the radiation image to the console device 16. However, a radiation image can be transmitted from the second electronic cassette 15B via the cradle unit 21 to the console device 16.

Also, it is possible to transmit information of completion of the reception from the second electronic cassette 15B to the first electronic cassette 15A upon the completion of receiving radiation images from the first electronic cassette 15A. It is possible in the first electronic cassette 15A to display information of readiness for subsequent imaging. To this end, a state indicator is incorporated in the first electronic cassette 15A. In case the first electronic cassette 15A receives information of the completion of the reception of images from the second electronic cassette 15B, the state indicator is turned on to inform the readiness for the subsequent imaging. This is effective in clarifying the readiness of the first electronic cassette 15A for the operation.

Furthermore, information of the available memory space in the memory can be acquired as first state information in the manner of the first embodiment, without the use of receiving the information of the changeover of the mode. One of the electronic cassettes 15 for use in the longitudinal imaging can be the second electronic cassette 15B in which the available memory space in the memory 67 is equal to or more than space threshold and also is the largest among the electronic cassettes 15.

Fourth Embodiment

In the above embodiments, the operator OP manually selects the electronic cassette 15 for use in the imaging. An error is likely to occur in selecting the electronic cassette 15 in relation to suitability for the imaging condition (menu for the object). In a fourth embodiment, the electronic cassette 15 has a function of selecting the electronic cassette 15 suitable for the imaging condition. The embodiment is described in relation to the imaging in the examination room 18 in FIG. 18.

Figure 25:
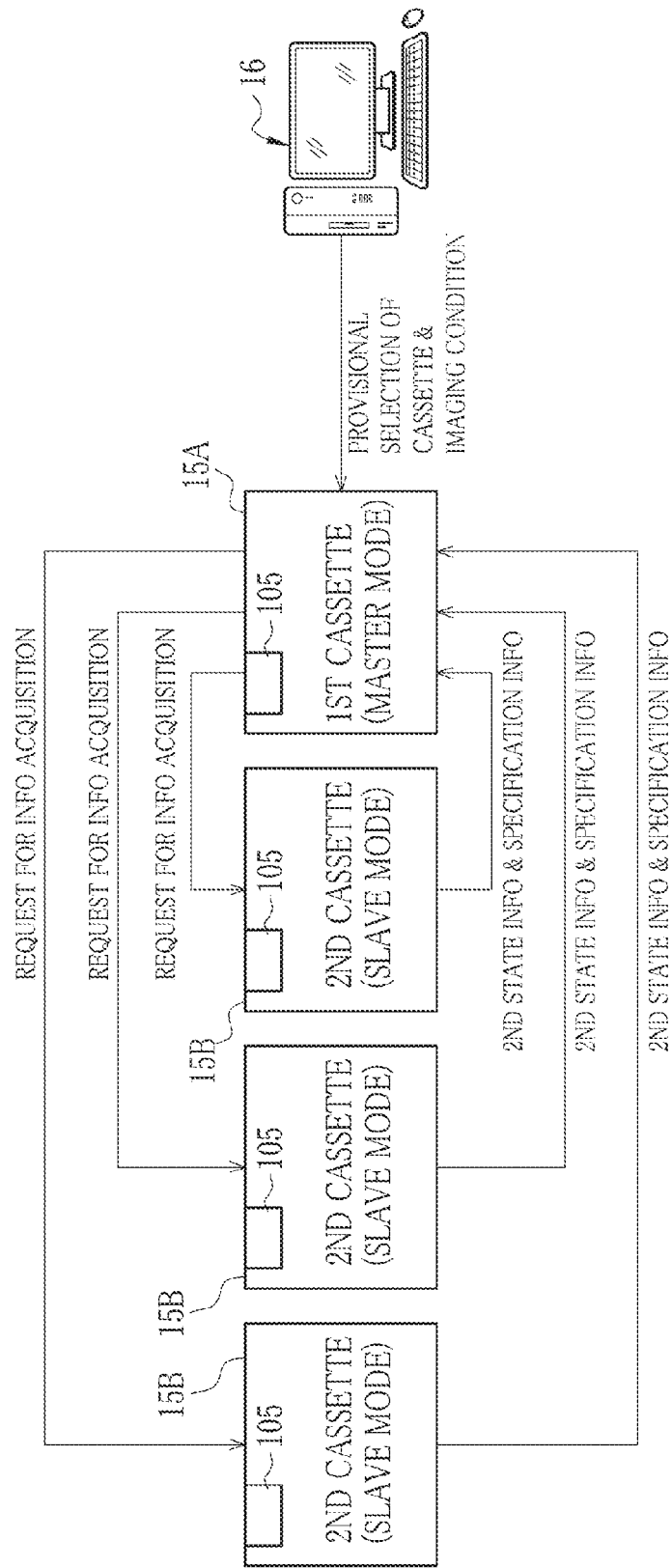
FIG. 25 is a block diagram schematically illustrating radio communication in a fourth preferred embodiment to transmit second state information and specification information.

In FIG. 25, the operator OP checks information of the request for imaging by viewing the console device 16 for imaging in the examination room 18, in the same manner as the above embodiments. The electronic cassette 15 for use is provisionally selected among the plural electronic cassettes 15 stored in the cradle unit 21 (not shown in FIG. 25). This is referred to as "provisional selection", because the electronic cassette 15 for use in the imaging becomes finally selected by the function in the electronic cassette 15 itself.

Then the operator OP selects the imaging condition. The console device 16 transmits the imaging condition and the exposure condition to the electronic cassette 15 selected provisionally via the cradle unit 21.

The radio communication unit 42 in the electronic cassette 15 upon receiving the imaging condition (menu for the object) from the console device 16 is set in the master mode and operates as an access point. The console device 16 performs the connecting sequence in FIG. 10 to establish a communication link with the second electronic cassette 15 of which the radio communication unit 42 operates in the slave mode in the cradle unit 21. In the embodiment, the electronic cassette 15 of which the radio communication unit 42 is the access point is the first electronic cassette 15A. The other electronic cassette in the slave mode is the second electronic cassette 15B, in the same manner as the first and second embodiments.

After establishing the communication link, the first electronic cassette 15A transmits a request for the information acquisition to the second electronic cassette 15B. The first electronic cassette 15A acquires the second state information and specification information generated by the second electronic cassette 15B in response to the request the information acquisition. The first electronic cassette 15A selects a main cassette (cassette for use) among the electronic cassettes 15 contained in the cradle unit 21 for imaging suitably for the imaging condition, on the basis of the second state information and specification information.

An indicator 105 is incorporated in each of the first and second electronic cassettes 15A and 15B and indicates a status of being selected as the main cassette. The indicator 105 is turned on upon the selection as the main cassette, and informs the operator OP of the selected status of the electronic cassette 15.

Assuming that the first electronic cassette 15A is selected itself as a functional cassette, the indicator 105 of the first electronic cassette 15A is turned on as illustrated in FIG. 26. Assuming that the second electronic cassette 15B is selected as a functional cassette, the first electronic cassette 15A transmits information of the functional cassette to the second electronic cassette 15B on as illustrated in FIG. 27. The indicator 105 of the second electronic cassette 15B is turned on.

In FIG. 26, the first electronic cassette 15A transmits the cassette ID to the console device 16. In FIG. 27, the first electronic cassette 15A transmits the cassette ID of the second electronic cassette 15B to the console device 16 after the selection of the main cassette (cassette for use). The console device 16 registers the cassette ID from the first electronic cassette 15A in the data item of the cassette ID in the request list 35.

In FIG. 28, a controller 110 of the electronic cassette 15 in the embodiment is operated to have a condition acquisition unit 111 (for event entry), a second data acquisition unit 112 (for monitoring functionality), a cassette selection unit 113 and a display processor 114 in addition to the cassette selection unit 82 (not shown) and the mode control unit 83.

The condition acquisition unit 111 acquires information of the imaging condition (menu for the object) and information of the exposure condition received by the wired communication interface 43 from the console device 16 via the cradle unit 21. The condition acquisition unit 111 outputs the received imaging condition and the like to the second data acquisition unit 112 and the cassette selection unit 113. The condition acquisition unit 111 outputs information of the provisional selection of the electronic cassette 15 to the mode control unit 83.

The radio communication unit 42 normally operates in the slave mode. The mode control unit 83 upon receiving information of the provisional selection from the condition acquisition unit 111 changes over the radio communication unit 42 from the slave mode to the master mode. Thus, the radio communication unit 42 operates as the access point.

The mode control unit 83 causes the second data acquisition unit 112 to acquire the second state information and the specification information upon receiving information of the provisional selection from the condition acquisition unit 111. The second data acquisition unit 112 outputs the request for information acquisition to the radio communication unit 42. The request is for instructing the second electronic cassette 15B wirelessly to transmit the second state information and specification information, and includes various data, such as information of the imaging condition (menu for the object) and information of the exposure condition from the condition acquisition unit 111.

The radio communication unit 42 wirelessly transmits the request for information acquisition from the second data acquisition unit 112 to the second electronic cassette 15B with the established communication link. The second electronic cassette 15B wirelessly transmits the second state information and specification information to the first electronic cassette 15A in response to the request, as illustrated in FIG. 25. The radio communication unit 42 receives the second state information and specification information from the second electronic cassette 15B. The second data acquisition unit 112 receives the second state information and specification information from the radio communication unit 42, and outputs the same to the cassette selection unit 113.

The cassette selection unit 113 selects the main cassette (cassette for use) according to the information of the imaging condition (menu for the object) from the condition acquisition unit 111, the second state information and specification information from the second data acquisition unit 112, and the recommended specification information read from the internal memory 84. The cassette selection unit 113 outputs the cassette ID of the main cassette to the wired communication interface 43. The wired communication interface 43 transmits the cassette ID of the main cassette to the console device 16 by cooperation of the cradle unit 21.

Assuming that the second electronic cassette 15B is selected as the main cassette, namely, assuming that the electronic cassette 15 other than the first electronic cassette 15A selected provisionally is selected, then the cassette selection unit 113 additionally outputs the cassette ID of the main cassette to the radio communication unit 42. The radio communication unit 42 transmits information of the main cassette to the second electronic cassette 15B of the cassette ID output by the cassette selection unit 113, to notify the selection as the main cassette. Assuming that the same cassette is selected as the main cassette, the cassette selection unit 113 outputs the information of the main cassette to the display processor 114.

The display processor 114 controls operation of the indicator 105. The display processor 114 turns on the indicator 105 upon receiving information of the main cassette (cassette for use) from the cassette selection unit 113 or the radio communication unit 42.

In FIG. 29, the second state information includes various data, such as the cassette ID of the second electronic cassette 15B, the available memory space of the memory 67, available time of the use of the battery 44, cumulative number of events of imaging, a date and time of correction updating (image detection for the offset correction) to detect an offset correction image for the purpose of the offset correction, and the like.

The offset correction is processing of removing original patterned noise from a radiation image due to specificity of the signal processor 66 or environment of the use of the electronic cassette 15. To this end, an offset correction image is prepared by image readout in the sensor panel 40 without irradiation of X-rays, and is subtracted from the radiation image by the unit of pixels.

The correction updating (image detection for the offset correction) is performed in case a main power source for the electronic cassette 15 at the start of the service in the hospital facility, or in case there is a difference in the environment of using the electronic cassette 15 from the former time of detecting the offset correction image, or the like. The offset correction image and information of the data and time of performing the correction updating are stored in the internal memory 84.

In FIG. 30, the specification information includes the cassette ID, outer size and pixel number of the second electronic cassette 15B. In FIG. 31, the recommended specification information is a set of data of recommended outer size and pixel number of the electronic cassette 15 for the respective imaging conditions.

In FIG. 32, a second information list 120 is produced by the cassette selection unit 113 and contains the second state information and the specification information in association with the respective cassette IDs. The cassette selection unit 113 registers not only the second state information and the specification information from the second electronic cassettes 15B but also those from the first electronic cassette 15A to the second information list 120. In FIG. 32, the second state information and the specification information of the cassettes with the cassette IDs of DR0002, DR0003 and DR0004 are associated with the second electronic cassettes 15B. The second state information and the specification information of the cassette with the cassette ID of DR0001 are associated with the first electronic cassette 15A.

In FIG. 33, a score list 121 is produced by the cassette selection unit 113 according to the second information list 120 and the recommended specification information. The score list 121 is information of registered scores for the respective data items of the second state information and specification information.

The score for the available memory space of the memory 67 is in a sequence of 10, 7, 4 and 1 in a decreasing manner according to the decrease of the available memory space. In FIG. 33, the second electronic cassette 15B of the cassette ID of DR0003 has the available memory space of 500 MB as the largest among the cassettes. The second electronic cassette 15B of the cassette ID of DR0002 has the available memory space of 200 MB. The second electronic cassette 15B of the cassette ID of DR0001 has the available memory space of 150 MB. The second electronic cassette 15B of the cassette ID of DR0004 has the available memory space of 20 MB. Thus, the registered score is 10 for the cassette ID of DR0003, 7 for the cassette ID of DR0002, 4 for the cassette ID of DR0001, and 1 for the cassette ID of DR0004.

A score related to the available time of the battery 44 is a decreasing value according to a decrease in the available time. A score related to the outer size and pixel number in the specification information is 10 for equality with the recommended outer size and recommended pixel number in the recommended specification information associated with the imaging condition (menu for the object) from the condition acquisition unit 111, and is 0 for inequality with the same. Note that a score (not shown) related to the cumulative number of events of imaging is decreased according to an increase in the cumulative number. A score (not shown) related to a date and time of detection of the offset correction image is decreased according to an increase in an interval between the date and time and the present date and time.

The cassette selection unit 113 adds up the registered scores for data items in the second state information and specification information, to obtain the total score for the respective cassette IDs. The cassette selection unit 113 outputs one of the cassette IDs with the highest total score as a cassette ID of the main cassette. In FIG. 33, "52" as the total score of the cassette ID of DR0002 is the highest. Then DR0002 as the cassette ID of the main cassette is output. This is effective in raising possibility of selecting the electronic cassette 15 as a main cassette from the electronic cassette 15 of which the available memory space of the memory 67 is relatively large, of which the available time of use of the battery 44 is relatively long, of which the cumulative number of events of imaging is relatively low, of which detection of the offset correction image has been considerably recently, and of which the outer size and pixel number are equal to the recommended outer size and recommended pixel number.

The operation of the embodiment is described now by referring to the flow of FIG. 34. At first, the electronic cassette 15 is provisionally selected in the console device 16 in a step S200. Then the imaging condition (menu for the object) is determined in a step S210. Information of the imaging condition and the exposure condition associated therewith is transmitted to the first electronic cassette 15A of the provisional selection via the cradle unit 21.

The imaging condition (menu for the object) from the console device 16 is received by the wired communication interface 43 in the first electronic cassette 15A in a step S300. Information of the imaging condition is acquired by the condition acquisition unit 111 (for event entry). The condition acquisition unit 111 outputs the information of the imaging condition (menu for the object) to the second data acquisition unit 112 (for monitoring functionality) and the cassette selection unit 113.

Also, the condition acquisition unit 111 outputs information of the provisional selection to the mode control unit 83. The mode control unit 83 upon the receipt changes over the radio communication unit 42 to the master mode, for operation as the access point in a step S310. In the second electronic cassette 15B, the radio communication unit 42 receives a beacon from the radio communication unit 42 of the first electronic cassette 15A, to establish a communication link between the first and second electronic cassettes 15A and 15B in the connecting sequence of FIG. 10, in a step S400.

The second data acquisition unit 112 outputs a request for the information acquisition to the radio communication unit 42, which wirelessly transmits the request to the second electronic cassette 15B in a step S320.

The second electronic cassette 15B receives a request for information acquisition from the first electronic cassette 15A in a step S410. In response to receiving the request, the second electronic cassette 15B wirelessly transmits the second state information and specification information to the first electronic cassette 15A in a step S420.

The first electronic cassette 15A receives the second state information and specification information from the second electronic cassette 15B in a step S330. In the first electronic cassette 15A, the second data acquisition unit 112 acquires the information. The second data acquisition unit 112 outputs the second state information and the specification information to the cassette selection unit 113.

The cassette selection unit 113 produces the second information list 120 in which the second state information and specification information are arranged for the respective cassette IDs, and produces the score list 121 of registered scores predetermined for the respective data items in the second state information and specification information. A total score of the respective cassette IDs is determined. One of the electronic cassettes 15 of which the total score is the highest is selected as a main cassette (cassette for use) in a step S340.

Assuming that the first electronic cassette 15A selected provisionally as main cassette is selected finally (yes in a step S350), the cassette selection unit 113 outputs information of the main cassette to the display processor 114 in a step S360. The indicator 105 in the first electronic cassette 15A is turned on in a step S370, to inform the operator OP of the selection of the first electronic cassette 15A for the main cassette.

Assuming that the second electronic cassette 15B is selected as the main cassette (cassette for use) (no in the step S350), the cassette selection unit 113 outputs the cassette ID of the main cassette to the radio communication unit 42. Thus, the radio communication unit 42 transmits information of the main cassette to the second electronic cassette 15B of the cassette ID output by the cassette selection unit 113, in a step S380.

Assuming that the second electronic cassette 15B receives information of the main cassette from the first electronic cassette 15A (yes in a step S430), the indicator 105 of the second electronic cassette 15B is turned on in a step S440, to inform the operator OP of the selection of the second electronic cassette 15B for the main cassette.

After selecting the main cassette (cassette for use), the first electronic cassette 15A transmits the cassette ID of the main cassette to the console device 16 in a step S390. The console device 16 receives the cassette ID, to register the cassette ID for a data item of the cassette ID in the request list 35, which is updated in a step S220.

After determining the imaging condition (menu for the object), the operator OP takes out the electronic cassette 15 from the cradle unit 21 in a turn-on state of the indicator 105 among the plural electronic cassettes 15 in the cradle unit 21, and sets the electronic cassette 15 on the floor stand 91 or the patient table 92. Succeeding steps of the embodiment are the same as those in the second embodiment.

Consequently, it is possible to select the most suitable one of the electronic cassettes 15 for the imaging condition (menu for the object), because a communication link is established between the first and second electronic cassettes 15A and 15B and the second state information and specification information of the second electronic cassette 15B is collected for the first electronic cassette 15A, to select the first electronic cassette 15A according to the imaging condition, the second state information and the specification information. The operator OP can perform decision for selecting the electronic cassette 15 without embarrassment. The radiographic imaging can be performed smoothly.

The second state information includes information of the available memory space of the memory 67 in the second electronic cassette 15B and information of available time of the use of the battery 44 in the second electronic cassette 15B. The second electronic cassette 15B which has a relatively large value of the available memory space and relatively long value of the available time can be selected as a main cassette. It is possible during the imaging to prevent incidental interruption of the imaging, for example, due to shortage in the available memory space of the memory 67 or use-up of the battery 44.

The indicator 105 for selection as the main cassette (cassette for use) makes it possible for the operator OP easily to recognize the main cassette. Also, a use of an unselected cassette different from the main cassette for the purpose of radiographic imaging can be prevented.

In the embodiment, the electronic cassette 15 is provisionally selected by the operator OP for transmission of the imaging condition (menu for the object) to the electronic cassette 15. Furthermore, an imaging condition and other information can be transmitted to a certain one of the plural electronic cassettes 15 stored in the cradle unit 21. The certain electronic cassette can be a first electronic cassette 15 placed in the cradle unit 21 the earliest among the plural electronic cassettes 15, and can be a specific electronic cassette 15 placed in a specific one of the receiving slots in the cradle unit 21. The radio communication unit 42 in the electronic cassette 15 receiving the imaging condition and the other information comes to operate as an access point, for the electronic cassette 15 to be the first electronic cassette 15A.

In the present embodiment, the imaging is performed in the examination room 18 in FIG. 18. However, the feature of the embodiment can be combined with the mobile imaging of the electronic cassette 15 of which selection is performed.

Furthermore, the second data acquisition unit 112 can be constituted by a first acquisition device and a second acquisition device, the first acquisition device acquiring the second state information, the second acquisition device (specification acquisition device) acquiring the specification information.

Also, the second state information and the specification information may include information other than described above. The score can be predetermined in a manner other than the above-described manner. Furthermore, determination of the score can be omitted. One of the electronic cassettes 15 of which the available memory space of the memory 67 is relatively large and of which the available time of the use of the battery 44 is relatively long can be selected as a main cassette, without determining the score.

In the embodiments, the console device 16 transmits the imaging condition (menu for the object) and the like to the electronic cassette 15. However, a sender for the imaging condition to the electronic cassette 15 is not limited to the console device 16. For example, portable information terminal equipment carried by the operator OP can be a sender for the imaging condition. Examples of the portable information terminal equipment are a mobile telephone, smart phone, tablet computer, PDA (Personal Digital Assistant), notebook computer, and other portable terminal devices.

In combination with the portable information terminal equipment, the electronic cassette 15 may not be directly connected to the console device 16 by the cradle unit 21 or the like. For this structure, at first the portable information terminal equipment becomes connected to the console device 16 in the storage room 17 in a wired manner or wirelessly. The request list 35 is downloaded from the console device 16 to the portable information terminal equipment. Then the electronic cassette 15 becomes connected to the portable information terminal equipment in a wired manner or wirelessly in the examination room 18 or the patient room 20. An imaging condition (menu for the object) and the like in the request list 35 are transferred from the portable information terminal equipment to the electronic cassette 15. Thus, it is unnecessary to provide the cradle unit 21 in the examination room 18. It is unnecessary to print the request list 35 on a paper material for the purpose of mobile imaging in the manner of the first embodiment.

Note that the radiographic imaging apparatus of the fourth embodiment can be changed over between the normal and relay transmission modes described in relation to the first embodiment. For example, assuming that the normal transmission mode is unavailable after selection of the first electronic cassette as a main cassette, the radiation image is transmitted from the first electronic cassette via the second electronic cassette to the console device. Assuming that the normal transmission mode is unavailable after selection of the second electronic cassette as a main cassette, the radiation image is transmitted from the second electronic cassette via the first electronic cassette to the console device.

Furthermore, the radiographic imaging apparatus of the fourth embodiment can be constructed for operation only in the normal transmission mode without providing the relay transmission mode.

Furthermore, the use of the portable information terminal equipment is effective remarkably in a situation depicted in FIG. 35.

In FIG. 35, a hospital facility has a first storage room 17A or preparation room, a first examination room 18A, a second storage room 17B or preparation room, and a second examination room 18B. The console devices 16A and 16B are installed in respectively the first and second storage rooms 17A and 17B. Cradle units 21A and 21B or charging cradles are installed in respectively the first and second examination rooms 18A and 18B. The cradle unit 21A in the first examination room 18A does not presently contain the electronic cassette 15.

At first, the operator OP downloads the request list 35 to portable information terminal equipment 130 from the console device 16A in the first storage room 17A. He or she moves from the first storage room 17A to the first examination room 18A with the portable information terminal equipment 130, and transfers the imaging condition (menu for the object) from the portable information terminal equipment 130 to one of the electronic cassettes 15 stored in the cradle unit 21B.

The electronic cassette 15 after transfer of the imaging condition and the like from the portable information terminal equipment 130 operates as the first electronic cassette 15A of the fourth embodiment, and selects a main cassette among the plural electronic cassettes 15 contained in the cradle unit 21B. The indicator 105 of the electronic cassette 15 selected as the main cassette is turned on. The operator OP takes out the electronic cassette 15 from the cradle unit 21B after checking the turn-on state of the indicator 105. Radiographic imaging is performed in the first examination room 18A after placement of the electronic cassette 15 therein.

Thus, the use of the portable information terminal equipment 130 enables the radiographic imaging by selecting the main cassette from the plural electronic cassettes 15 in the cradle unit 21B in the second examination room 18B assuming that the electronic cassette 15 is not stored in the cradle unit 21A in the first examination room 18A.

For this structure, a cassette ID of the main cassette is transmitted to the portable information terminal equipment 130 at first. The request list 35 is updated in the portable information terminal equipment 130. Upon the return to the first storage room 17A, the request list 35 of the updated form is transmitted back to the console device 16 by the portable information terminal equipment 130. The console device 16 abandons the earlier information in the request list 35, and stores the request list 35 of the updated form from the portable information terminal equipment 130.

Various modifications of the embodiments are possible in the scope of the present invention. For example, the first and second electronic cassettes 15A and 15B can communicate with each other in an ad hoc mode wirelessly instead of using the infrastructure mode in combination of the access point of relay.

Features of two or more of the above-described embodiments can be combined with one another. Also, radiation for use in the radiographic imaging can be gamma rays or the like instead of X-rays.

In a preferred embodiment mode of the invention, a radiographic imaging method is provided, and includes a step of detecting a radiation image of an object by use of one of first and second electronic cassettes, to input the radiation image to the console device. The first electronic cassette is changed over between a normal transmission mode and a relay transmission mode, wherein in the normal transmission mode, the radiation image is transmitted through a path from the first electronic cassette to the console device, and in the relay transmission mode, the radiation image is transmitted from the first electronic cassette to the second electronic cassette wirelessly and then from the second electronic cassette to the console device.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiographic imaging apparatus comprising:
    a console device;
    a first electronic cassette, connected with said console device communicably, for generating a radiation image of an object by detecting radiation passed through said object, to transmit said radiation image to said console device;
    a second electronic cassette, connected with said console device communicably, connected wirelessly with said first electronic cassette communicably, for generating a radiation image of an object by detecting radiation passed through said object, to transmit said radiation image to said console device;
    a mode control unit for changing over said first electronic cassette between a normal transmission mode and a relay transmission mode, wherein in said normal transmission mode, said radiation image is transmitted through a path from said first electronic cassette to said console device, and in said relay transmission mode, said radiation image is transmitted from said first electronic cassette to said second electronic cassette wirelessly and then from said second electronic cassette to said console device.

2. A radiographic imaging apparatus as defined in claim 1, wherein said mode control unit, in case said first electronic cassette is in a predetermined specific state, sets said relay transmission mode, and in case said first electronic cassette is in a state different from said specific state, sets said normal transmission mode.

3. A radiographic imaging apparatus as defined in claim 2, wherein said first electronic cassette includes a memory for temporarily storing said radiation image;
    said specific state is a state of shortage in an available memory space in said memory, or a state of unavailability of said normal transmission mode.

4. A radiographic imaging apparatus as defined in claim 3, wherein said second electronic cassette is constituted by plural second electronic cassettes;
    said first electronic cassette includes:

a first data acquisition unit for acquiring first state information of a state of said second electronic cassettes from respectively said plural second electronic cassettes;

a cassette selection unit for determining a functional cassette among said plural second electronic cassettes according to said first state information for wirelessly transmitting said radiation image in said relay transmission mode.

5. A radiographic imaging apparatus as defined in claim 4, wherein said second electronic cassette includes a memory for temporarily storing said radiation image;

said first state information is related to an available memory space in said memory, or connectivity of said second electronic cassette with said console device;

said cassette selection unit determines said functional cassette from said second electronic cassette having said available memory space sufficient for storing said radiation image, or which is communicable with said console device in said connectivity.

6. A radiographic imaging apparatus as defined in claim 4, wherein said functional cassette upon receiving said radiation image from said first electronic cassette transmits original sender information to said console device for expressing said first electronic cassette for a sender of said radiation image so as to transmit said radiation image to said console device.

7. A radiographic imaging apparatus as defined in claim 5, wherein said second electronic cassette is operable as an access point, and said access point in said functional cassette transmits said radiation image to said console device.

8. A radiographic imaging apparatus as defined in claim 4, wherein said first electronic cassette is operable as an access point, and said access point wirelessly communicates with said second electronic cassette, and receives said first state information.

9. A radiographic imaging apparatus as defined in claim 2, wherein said specific state is a state of longitudinal imaging for a continuous region including plural body parts of said object by combining said first and second electronic cassettes.

10. A radiographic imaging apparatus as defined in claim 9, wherein in said state of said longitudinal imaging, said mode control unit sets said relay transmission mode in said first electronic cassette, to transmit said radiation image wirelessly to said second electronic cassette;

said radiation images from said first and second electronic cassettes are transmitted together from said second electronic cassette to said console device.

11. A radiographic imaging apparatus as defined in claim 1, further comprising a cassette selection unit for selecting a main cassette for use in said imaging among said first and second electronic cassettes according to comparison of information of said first and second electronic cassettes.

12. A radiographic imaging apparatus as defined in claim 11, wherein said first electronic cassette includes:

a condition acquisition unit for acquiring an imaging condition determined according to a request for imaging;

a data acquisition unit for acquiring state information of a state of said second electronic cassette;

a specification acquisition device for acquiring specification information of said second electronic cassette;

wherein said cassette selection unit operates according to said imaging condition, said state information and said specification information.

13. A radiographic imaging apparatus as defined in claim 12, wherein said second electronic cassette includes a memory for temporarily storing said radiation image;

said state information is at least related to an available memory space in said memory and available time of use of a battery for powering said second electronic cassette.

14. A radiographic imaging apparatus as defined in claim 12, wherein each of said first and second electronic cassettes includes an indicator for indicating information of selection of said main cassette in said cassette selection unit.

15. An electronic cassette, connected with a console device communicably, for generating a radiation image of an object by detecting radiation passed through said object, to transmit said radiation image to said console device, comprising:

a radio communication unit for wirelessly communicating with an external electronic cassette;

a mode control unit for changing over between a normal transmission mode and a relay transmission mode, wherein in said normal transmission mode, said radiation image is transmitted through a path to said console device, and in said relay transmission mode, said radiation image is transmitted from said radio communication unit to said external electronic cassette and then from said external electronic cassette to said console device.

* * * * *